(12) United States Patent
Fette

(10) Patent No.: US 11,938,246 B2
(45) Date of Patent: Mar. 26, 2024

(54) TISSUE-BASED COMPOSITIONS AND METHODS OF USE THEREOF

(71) Applicant: FETTECH, LLC, Davie, FL (US)

(72) Inventor: Clay Fette, Davie, FL (US)

(73) Assignee: FETTECH, LLC, Davie, FL (US)

( * ) Notice: Subject to any disclaimer, the term of this patent is extended or adjusted under 35 U.S.C. 154(b) by 352 days.

(21) Appl. No.: 17/144,739

(22) Filed: Jan. 8, 2021

(65) Prior Publication Data

US 2021/0308328 A1    Oct. 7, 2021

Related U.S. Application Data

(63) Continuation of application No. 14/963,571, filed on Dec. 9, 2015, now abandoned, which is a continuation of application No. 14/582,288, filed on Dec. 24, 2014, now Pat. No. 9,238,090.

(51) Int. Cl.
*A61L 27/36* (2006.01)
*A61L 27/54* (2006.01)
*A61L 27/56* (2006.01)

(52) U.S. Cl.
CPC ........... *A61L 27/3633* (2013.01); *A61L 27/54* (2013.01); *A61L 27/56* (2013.01); *A61L 2300/104* (2013.01); *A61L 2300/404* (2013.01); *A61L 2300/414* (2013.01)

(58) Field of Classification Search
CPC .................. A61L 2300/414; A61L 27/3633
See application file for complete search history.

(56) References Cited

U.S. PATENT DOCUMENTS

| | | |
|---|---|---|
| 4,587,268 A | 5/1986 | Pfirrmann |
| 4,599,226 A | 7/1986 | Fox, Jr. et al. |
| 4,801,299 A | 1/1989 | Brendel et al. |
| 4,847,049 A | 7/1989 | Yamamoto |
| 4,880,429 A | 11/1989 | Stone |
| 4,902,508 A | 2/1990 | Badylak et al. |
| 4,925,924 A | 5/1990 | Silver et al. |
| 4,956,178 A | 9/1990 | Badylak et al. |
| 5,081,106 A | 1/1992 | Bentley et al. |
| 5,162,430 A | 11/1992 | Rhee et al. |
| 5,196,185 A | 3/1993 | Silver et al. |
| 5,197,977 A | 3/1993 | Hoffman, Jr. et al. |
| 5,275,826 A | 1/1994 | Badylak et al. |
| 5,281,422 A | 1/1994 | Badylak et al. |
| 5,290,763 A | 3/1994 | Poser et al. |
| 5,294,446 A | 3/1994 | Schlameus et al. |
| 5,300,306 A | 4/1994 | Alvarado et al. |
| 5,326,357 A | 7/1994 | Kandel |
| 5,352,463 A | 10/1994 | Badylak et al. |
| 5,372,821 A | 12/1994 | Badylak et al. |
| 5,374,515 A | 12/1994 | Parenteau et al. |
| 5,445,833 A | 8/1995 | Badylak et al. |
| 5,456,693 A | 10/1995 | Conston et al. |
| 5,460,962 A | 10/1995 | Kemp |
| 5,466,462 A | 11/1995 | Rosenthal et al. |
| 5,510,263 A | 4/1996 | Quaranta et al. |
| 5,554,389 A | 9/1996 | Badylak et al. |
| 5,573,784 A | 11/1996 | Badylak et al. |
| 5,595,571 A | 1/1997 | Jaffe et al. |
| 5,641,518 A | 6/1997 | Badylak et al. |
| 5,645,860 A | 7/1997 | Knapp, Jr. et al. |
| 5,665,114 A | 9/1997 | Weadock et al. |
| 5,693,085 A | 12/1997 | Buirge et al. |
| 5,700,477 A | 12/1997 | Rosenthal et al. |
| 5,709,934 A | 1/1998 | Bell et al. |
| 5,711,969 A | 1/1998 | Patel et al. |
| 5,723,010 A | 3/1998 | Yui et al. |
| 5,733,337 A | 3/1998 | Carr, Jr. et al. |
| 5,755,791 A | 5/1998 | Whitson et al. |
| 5,800,537 A | 9/1998 | Bell |
| 5,804,213 A | 9/1998 | Rolf |
| 5,819,748 A | 10/1998 | Pfirrmann |
| 5,873,904 A | 2/1999 | Ragheb et al. |
| 5,876,451 A | 3/1999 | Yui et al. |
| 5,885,619 A | 3/1999 | Patel et al. |
| 5,893,888 A | 4/1999 | Bell |
| 5,895,419 A | 4/1999 | Tweden et al. |
| 5,902,228 A | 5/1999 | Schulsinger et al. |
| 5,922,028 A | 7/1999 | Plouhar et al. |
| 5,948,429 A | 9/1999 | Bell et al. |
| 5,955,110 A | 9/1999 | Patel et al. |
| 5,965,125 A | 10/1999 | Mineau-Hanschke |
| 5,968,096 A | 10/1999 | Whitson et al. |
| 5,993,844 A | 11/1999 | Abraham et al. |
| 5,997,575 A | 12/1999 | Whitson et al. |
| 6,022,557 A | 2/2000 | Maser |
| 6,051,750 A | 4/2000 | Bell |
| 6,054,122 A | 4/2000 | MacPhee et al. |
| 6,087,549 A | 7/2000 | Flick |
| 6,099,567 A | 8/2000 | Badylak et al. |

(Continued)

FOREIGN PATENT DOCUMENTS

| | | |
|---|---|---|
| EP | 0773033 A1 | 5/1997 |
| EP | 0781564 A2 | 7/1997 |

(Continued)

OTHER PUBLICATIONS

Bhan, C. et al., "Adsorption-Desorption Study of BSA Conjugated Silver Nanoparticles (Ag/BSA NPs) on Collagen Immobilized Substrates," *Langmuir*, vol. 28, No. 49, pp. 17043-17052 (2012) (abstract only).

(Continued)

*Primary Examiner* — Thane Underdahl
(74) *Attorney, Agent, or Firm* — Bookoff McAndrews PLLC

(57) ABSTRACT

Compositions comprising extracellular matrix (ECM) materials and methods of use thereof are disclosed. The compositions may comprise two or more ECM materials derived from different types of tissues, such as, e.g., lung tissue and spleen tissue, formulated for administration to a patient or configured as a medical device for implantation in or application to the patient. The compositions may combine complementary properties of different types of ECM materials for customized patient-specific and/or site-specific tissue repair and/or regeneration.

19 Claims, 4 Drawing Sheets

(56) References Cited

U.S. PATENT DOCUMENTS

| | | |
|---|---|---|
| 6,110,208 A | 8/2000 | Soranzo et al. |
| 6,113,636 A | 9/2000 | Ogle |
| 6,124,273 A | 9/2000 | Drohan et al. |
| 6,129,757 A | 10/2000 | Weadock |
| 6,152,964 A | 11/2000 | Van Blitterswijk et al. |
| 6,153,292 A | 11/2000 | Bell et al. |
| 6,171,344 B1 | 1/2001 | Atala |
| 6,179,872 B1 | 1/2001 | Bell et al. |
| 6,197,935 B1 | 3/2001 | Doillon et al. |
| 6,206,931 B1 | 3/2001 | Cook et al. |
| 6,281,007 B1 | 8/2001 | Fofonoff et al. |
| 6,334,872 B1 | 1/2002 | Termin et al. |
| 6,358,284 B1 | 3/2002 | Fearnot et al. |
| 6,368,859 B1 | 4/2002 | Atala |
| 6,376,244 B1 | 4/2002 | Atala |
| 6,398,819 B1 | 6/2002 | Bell |
| 6,432,436 B1 | 8/2002 | Gertzman et al. |
| 6,458,889 B1 | 10/2002 | Trollsas et al. |
| 6,485,723 B1 | 11/2002 | Badylak et al. |
| 6,485,969 B1 | 11/2002 | Asem et al. |
| 6,503,539 B2 | 1/2003 | Gestrelius et al. |
| 6,509,145 B1 | 1/2003 | Torrianni |
| 6,511,958 B1 | 1/2003 | Atkinson et al. |
| 6,530,951 B1 | 3/2003 | Bates et al. |
| 6,576,015 B2 | 6/2003 | Geistlich et al. |
| 6,576,265 B1 | 6/2003 | Spievack |
| 6,579,538 B1 | 6/2003 | Spievack |
| 6,585,754 B2 | 7/2003 | Wallace et al. |
| 6,592,794 B1 | 7/2003 | Bachrach |
| 6,599,690 B1 | 7/2003 | Abraham et al. |
| 6,638,312 B2 | 10/2003 | Plouhar et al. |
| 6,666,892 B2 | 12/2003 | Hiles et al. |
| 6,673,339 B1 | 1/2004 | Atala et al. |
| 6,719,987 B2 | 4/2004 | Burrell et al. |
| 6,753,181 B2 | 6/2004 | Atala |
| 6,783,776 B2 | 8/2004 | Spievack |
| 6,812,217 B2 | 11/2004 | Hendriks |
| 6,849,273 B2 | 2/2005 | Spievack |
| 6,852,339 B2 | 2/2005 | Spievack |
| 6,861,074 B2 | 3/2005 | Spievack |
| 6,869,619 B2 | 3/2005 | Spievack |
| 6,881,766 B2 | 4/2005 | Hain |
| 6,882,880 B2 | 4/2005 | Treppo et al. |
| 6,887,495 B2 | 5/2005 | Spievack |
| 6,890,351 B2 | 5/2005 | Termin et al. |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 6,933,326 B1 | 8/2005 | Griffey et al. |
| 6,939,369 B2 | 9/2005 | Osborne et al. |
| 6,974,474 B2 | 12/2005 | Pavcnik et al. |
| 7,056,337 B2 | 6/2006 | Boatman |
| 7,056,533 B2 | 6/2006 | Chudzik et al. |
| 7,060,103 B2 | 6/2006 | Carr, Jr. et al. |
| 7,087,089 B2 | 8/2006 | Patel et al. |
| 7,105,001 B2 | 9/2006 | Mandelbaum |
| 7,121,999 B2 | 10/2006 | Abraham et al. |
| 7,153,324 B2 | 12/2006 | Case et al. |
| 7,153,518 B2 | 12/2006 | Wironen et al. |
| 7,160,333 B2 | 1/2007 | Plouhar et al. |
| 7,163,563 B2 | 1/2007 | Schwartz et al. |
| 7,175,841 B2 | 2/2007 | Badylak et al. |
| 7,201,917 B2 | 4/2007 | Malaviya et al. |
| 7,211,275 B2 | 5/2007 | Ying et al. |
| 7,238,198 B2 | 7/2007 | Hartley et al. |
| 7,244,444 B2 | 7/2007 | Bates |
| 7,252,832 B1 | 8/2007 | Stone et al. |
| 7,316,822 B2 | 1/2008 | Binette et al. |
| 7,326,571 B2 | 2/2008 | Freyman |
| 7,335,228 B2 | 2/2008 | Schaeffer |
| 7,354,627 B2 | 4/2008 | Pedrozo et al. |
| 7,410,502 B2 | 8/2008 | Ellingsen et al. |
| 7,458,987 B2 | 12/2008 | Case et al. |
| 7,524,332 B2 | 4/2009 | Osborne et al. |
| 7,569,233 B2 | 8/2009 | Malaviya et al. |
| 7,579,189 B2 | 8/2009 | Freyman et al. |
| 7,595,062 B2 | 9/2009 | Pedrozo et al. |
| 7,597,712 B2 | 10/2009 | Parenteau et al. |
| 7,615,373 B2 | 11/2009 | Simpson et al. |
| 7,622,129 B1 | 11/2009 | Haberstroh et al. |
| 7,666,829 B2 | 2/2010 | Mitts et al. |
| 7,691,140 B2 | 4/2010 | Bates et al. |
| 7,744,621 B2 | 6/2010 | Paul et al. |
| 7,753,955 B2 | 7/2010 | Wuh |
| 7,763,270 B2 | 7/2010 | Hellerbrand et al. |
| 7,776,596 B2 | 8/2010 | Badylak |
| 7,795,022 B2 | 9/2010 | Badylak |
| 7,795,027 B2 | 9/2010 | Hiles |
| 7,799,089 B2 | 9/2010 | Plouhar et al. |
| 7,815,923 B2 | 10/2010 | Johnson et al. |
| 7,820,172 B1 | 10/2010 | Zamora et al. |
| 7,833,267 B2 | 11/2010 | Flagle et al. |
| 7,851,445 B2 | 12/2010 | Stupp et al. |
| 7,857,825 B2 | 12/2010 | Moran et al. |
| 7,914,567 B2 | 3/2011 | Pavcnik et al. |
| 7,914,808 B2 | 3/2011 | Malaviya et al. |
| 7,919,112 B2 | 4/2011 | Pathak et al. |
| 7,959,554 B2 | 6/2011 | McAlexander et al. |
| 7,959,683 B2 | 6/2011 | Semler et al. |
| 8,003,131 B2 | 8/2011 | Badylak |
| 8,025,896 B2 | 9/2011 | Malaviya et al. |
| 8,029,532 B2 | 10/2011 | Sirota |
| 8,049,059 B2 | 11/2011 | Bleyer et al. |
| 8,057,528 B2 | 11/2011 | Parker |
| 8,066,733 B2 | 11/2011 | Paul et al. |
| 8,067,149 B2 | 11/2011 | Livesey et al. |
| 8,076,137 B2 | 12/2011 | McAllister et al. |
| 8,076,294 B2 | 12/2011 | Kinney et al. |
| 8,084,048 B2 | 12/2011 | Badylak |
| 8,128,682 B2 | 3/2012 | Case et al. |
| 8,142,475 B2 | 3/2012 | Viola |
| 8,211,165 B1 | 7/2012 | McIntosh et al. |
| 8,216,299 B2 | 7/2012 | Paul, Jr. et al. |
| 8,257,434 B2 | 9/2012 | Matheny |
| 8,263,101 B2 | 9/2012 | Owens et al. |
| 8,288,344 B2 | 10/2012 | DePaula |
| 8,298,586 B2 | 10/2012 | Bosley, Jr. et al. |
| 8,303,647 B2 | 11/2012 | Case |
| 8,303,648 B2 | 11/2012 | Grewe et al. |
| 8,317,823 B2 | 11/2012 | Pavcnik et al. |
| 8,329,202 B2 | 12/2012 | Venu et al. |
| 8,329,219 B2 | 12/2012 | Farrell et al. |
| 8,337,873 B2 | 12/2012 | Mao |
| 8,343,535 B2 | 1/2013 | Burd et al. |
| 8,343,536 B2 | 1/2013 | Bates et al. |
| 8,348,988 B2 | 1/2013 | Lad et al. |
| 8,354,501 B2 | 1/2013 | Kaplan et al. |
| 8,366,787 B2 | 2/2013 | Brown et al. |
| 8,372,140 B2 | 2/2013 | Hoffman et al. |
| 8,415,159 B2 | 4/2013 | Ward et al. |
| 8,431,148 B2 | 4/2013 | McKay |
| 8,445,016 B2 | 5/2013 | Santerre et al. |
| 8,454,678 B2 | 6/2013 | Hiles |
| 8,455,008 B2 | 6/2013 | Johnson |
| 8,465,516 B2 | 6/2013 | Pavcnik et al. |
| 8,470,356 B2 | 6/2013 | Patel et al. |
| 8,475,512 B2 | 7/2013 | Hunt |
| 8,529,951 B1 | 9/2013 | Ramamurthi et al. |
| 8,535,349 B2 | 9/2013 | Chen et al. |
| 8,535,719 B2 | 9/2013 | Badylak et al. |
| 8,540,760 B2 | 9/2013 | Paul, Jr. et al. |
| 8,541,032 B2 | 9/2013 | Bosley, Jr. et al. |
| 8,556,960 B2 | 10/2013 | Agnew et al. |
| 8,557,277 B2 | 10/2013 | Virkler et al. |
| 8,591,930 B2 | 11/2013 | Hiles et al. |
| 8,603,982 B2 | 12/2013 | Ooya et al. |
| 8,613,937 B2 | 12/2013 | Boyden et al. |
| 8,628,787 B2 | 1/2014 | Soldani et al. |
| 8,637,067 B1 | 1/2014 | Sun et al. |
| 8,641,776 B2 | 2/2014 | Case et al. |
| 8,647,677 B2 | 2/2014 | Badylak et al. |
| 8,652,191 B2 | 2/2014 | Fearnot et al. |

(56) References Cited

U.S. PATENT DOCUMENTS

| | | |
|---|---|---|
| 8,652,216 B2 | 2/2014 | Chen et al. |
| 8,658,196 B2 | 2/2014 | Janis |
| 8,673,019 B2 | 3/2014 | McKay |
| 8,685,432 B2 | 4/2014 | Evans et al. |
| 8,695,530 B2 | 4/2014 | Sun |
| 8,696,744 B2 | 4/2014 | Matheny et al. |
| 8,709,076 B1 | 4/2014 | Matheny et al. |
| 8,709,401 B2 | 4/2014 | Song |
| 8,728,463 B2 | 5/2014 | Atala et al. |
| 8,734,501 B2 | 5/2014 | Hartley et al. |
| 8,741,352 B2 | 6/2014 | Hodde et al. |
| 8,741,354 B2 | 6/2014 | Johnson et al. |
| 8,758,448 B2 | 6/2014 | Matheny |
| 8,778,012 B2 | 7/2014 | Matheny |
| 8,778,362 B2 | 7/2014 | Suckow et al. |
| 8,784,499 B2 | 7/2014 | Owens et al. |
| 8,784,889 B2 | 7/2014 | Hodde et al. |
| 8,785,198 B1 | 7/2014 | Matheny |
| 9,056,078 B2 | 6/2015 | Bosley, Jr. et al. |
| 2001/0014667 A1 | 8/2001 | Chen et al. |
| 2001/0020188 A1 | 9/2001 | Sander |
| 2001/0044650 A1 | 11/2001 | Simso et al. |
| 2001/0048949 A1 | 12/2001 | Atala |
| 2002/0001623 A1 | 1/2002 | Yamashita et al. |
| 2002/0038151 A1 | 3/2002 | Plouhar et al. |
| 2002/0055143 A1 | 5/2002 | Bell et al. |
| 2002/0082697 A1 | 6/2002 | Damien |
| 2002/0122816 A1 | 9/2002 | Sung et al. |
| 2002/0128722 A1 | 9/2002 | Jefferies |
| 2002/0150603 A1 | 10/2002 | Dionne et al. |
| 2003/0004568 A1 | 1/2003 | Ken et al. |
| 2003/0007991 A1 | 1/2003 | Masters |
| 2003/0023316 A1 | 1/2003 | Brown et al. |
| 2003/0026770 A1 | 2/2003 | Szymaitis |
| 2003/0032961 A1 | 2/2003 | Pelo et al. |
| 2003/0044444 A1 | 3/2003 | Malaviya et al. |
| 2003/0049299 A1 | 3/2003 | Malaviya et al. |
| 2003/0049839 A1 | 3/2003 | Romero-Ortega et al. |
| 2003/0143207 A1 | 7/2003 | Livesey et al. |
| 2003/0175410 A1 | 9/2003 | Campbell et al. |
| 2003/0194444 A1 | 10/2003 | Burrell et al. |
| 2003/0211601 A1 | 11/2003 | Atala |
| 2004/0054414 A1 | 3/2004 | Trieu et al. |
| 2004/0059431 A1 | 3/2004 | Plouhar et al. |
| 2004/0082063 A1 | 4/2004 | Deshpande et al. |
| 2004/0083006 A1 | 4/2004 | Ellingsen et al. |
| 2004/0131678 A1 | 7/2004 | Burger |
| 2004/0138758 A1 | 7/2004 | Evans et al. |
| 2004/0166169 A1 | 8/2004 | Malaviya et al. |
| 2004/0167634 A1 | 8/2004 | Atala et al. |
| 2004/0175366 A1 | 9/2004 | Badylak |
| 2004/0220574 A1 | 11/2004 | Pelo et al. |
| 2004/0229333 A1 | 11/2004 | Bowlin et al. |
| 2004/0267362 A1 | 12/2004 | Hwang et al. |
| 2005/0025838 A1 | 2/2005 | Badylak |
| 2005/0079200 A1 | 4/2005 | Rathenow et al. |
| 2005/0085924 A1 | 4/2005 | Darois et al. |
| 2005/0129730 A1 | 6/2005 | Pang et al. |
| 2005/0131517 A1 | 6/2005 | Hartley et al. |
| 2005/0163825 A1 | 7/2005 | Naidu |
| 2005/0201989 A1 | 9/2005 | Geliebter et al. |
| 2005/0249771 A1 | 11/2005 | Malaviya et al. |
| 2005/0249772 A1 | 11/2005 | Malaviya et al. |
| 2005/0260612 A1 | 11/2005 | Padmini et al. |
| 2006/0015052 A1 | 1/2006 | Crisp |
| 2006/0051396 A1 | 3/2006 | Hamilton et al. |
| 2006/0068032 A1 | 3/2006 | Zhao et al. |
| 2006/0074447 A2 | 4/2006 | Armstrong |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0136047 A1 | 6/2006 | Obermiller et al. |
| 2006/0147491 A1 | 7/2006 | DeWitt et al. |
| 2006/0155384 A1 | 7/2006 | Ellingsen et al. |
| 2006/0159664 A1 | 7/2006 | Pandit et al. |
| 2006/0198868 A1 | 9/2006 | DeWitt et al. |
| 2006/0201996 A1 | 9/2006 | Hodde |
| 2006/0216324 A1 | 9/2006 | Stucke et al. |
| 2006/0222635 A1 | 10/2006 | Centanni et al. |
| 2006/0240014 A1 | 10/2006 | Sukhatme |
| 2006/0246033 A1 | 11/2006 | Ninan |
| 2006/0263335 A1 | 11/2006 | France et al. |
| 2006/0275270 A1 | 12/2006 | Warren et al. |
| 2006/0293760 A1 | 12/2006 | DeDeyne |
| 2007/0009586 A1 | 1/2007 | Cohen et al. |
| 2007/0014755 A1 | 1/2007 | Beckman et al. |
| 2007/0015685 A1 | 1/2007 | Balaban |
| 2007/0098755 A1 | 5/2007 | Patel et al. |
| 2007/0112411 A1 | 5/2007 | Obermiller et al. |
| 2007/0128723 A1 | 6/2007 | Cottone et al. |
| 2007/0184122 A1 | 8/2007 | Johnson et al. |
| 2007/0196380 A1 | 8/2007 | Firestone |
| 2007/0213805 A1 | 9/2007 | Schaeffer et al. |
| 2007/0218038 A1 | 9/2007 | Nataraj et al. |
| 2007/0225663 A1 | 9/2007 | Watt et al. |
| 2007/0232561 A1 | 10/2007 | Leung et al. |
| 2007/0265346 A1 | 11/2007 | Mehta |
| 2007/0274962 A1 | 11/2007 | Lui |
| 2007/0276509 A1 | 11/2007 | Ratcliffe et al. |
| 2007/0299517 A1 | 12/2007 | Davisson et al. |
| 2008/0003330 A1 | 1/2008 | Rueda et al. |
| 2008/0038352 A1 | 2/2008 | Simpson et al. |
| 2008/0039927 A1 | 2/2008 | Barr |
| 2008/0081362 A1 | 4/2008 | Keeley et al. |
| 2008/0118551 A1 | 5/2008 | Wadia |
| 2008/0147038 A1 | 6/2008 | Hoffman |
| 2008/0147197 A1 | 6/2008 | McKay |
| 2008/0181951 A1 | 7/2008 | Holladay et al. |
| 2008/0243243 A1 | 10/2008 | Williams et al. |
| 2008/0248079 A1 | 10/2008 | Dempsey et al. |
| 2008/0260831 A1 | 10/2008 | Badylak et al. |
| 2008/0260853 A1 | 10/2008 | Firestone |
| 2008/0274184 A1 | 11/2008 | Hunt |
| 2008/0279939 A1 | 11/2008 | Firestone |
| 2008/0281418 A1 | 11/2008 | Firestone |
| 2008/0286329 A1 | 11/2008 | Campbell et al. |
| 2009/0017093 A1 | 1/2009 | Springer et al. |
| 2009/0035289 A1 | 2/2009 | Wagner et al. |
| 2009/0035356 A1 | 2/2009 | Bui-Khac et al. |
| 2009/0074871 A1 | 3/2009 | Sunwoo et al. |
| 2009/0130068 A1 | 5/2009 | Eklund |
| 2009/0142409 A1 | 6/2009 | Firestone et al. |
| 2009/0163936 A1 | 6/2009 | Yang et al. |
| 2009/0163990 A1 | 6/2009 | Yang et al. |
| 2009/0169593 A1 | 7/2009 | Gregory et al. |
| 2009/0175922 A1 | 7/2009 | Voytik-Harbin |
| 2009/0186332 A1 | 7/2009 | Manders et al. |
| 2009/0202434 A1 | 8/2009 | Da Cruz |
| 2009/0204228 A1 | 8/2009 | Hiles |
| 2009/0215009 A1 | 8/2009 | Noishiki et al. |
| 2009/0216336 A1 | 8/2009 | Springer et al. |
| 2009/0238853 A1 | 9/2009 | Liu et al. |
| 2009/0254104 A1 | 10/2009 | Murray |
| 2009/0311298 A1 | 12/2009 | Nixon et al. |
| 2009/0317441 A1 | 12/2009 | Bilbo et al. |
| 2010/0010627 A1 | 1/2010 | Matheny |
| 2010/0016872 A1 | 1/2010 | Bayon et al. |
| 2010/0021519 A1 | 1/2010 | Shenoy |
| 2010/0042091 A1 | 2/2010 | Shadduck |
| 2010/0047308 A1 | 2/2010 | Kim et al. |
| 2010/0047309 A1 | 2/2010 | Lu et al. |
| 2010/0080788 A1 | 4/2010 | Barnett et al. |
| 2010/0104652 A1 | 4/2010 | Biris et al. |
| 2010/0143490 A1 | 6/2010 | Roberts et al. |
| 2010/0172889 A1 | 7/2010 | Catchmark et al. |
| 2010/0189721 A1 | 7/2010 | L'Heureux et al. |
| 2010/0233140 A1 | 9/2010 | Just et al. |
| 2010/0239560 A1 | 9/2010 | Hassingboe et al. |
| 2010/0249830 A1 | 9/2010 | Nelson |
| 2010/0249927 A1 | 9/2010 | Yang et al. |
| 2010/0266654 A1 | 10/2010 | Hodde et al. |
| 2010/0268227 A1 | 10/2010 | Tong et al. |
| 2010/0272779 A1 | 10/2010 | Jackson |
| 2010/0291180 A1 | 11/2010 | Uhrich |

(56) References Cited

U.S. PATENT DOCUMENTS

| | | |
|---|---|---|
| 2010/0303722 A1 | 12/2010 | Jin et al. |
| 2010/0318193 A1 | 12/2010 | Desai et al. |
| 2010/0329995 A1 | 12/2010 | Deeter et al. |
| 2011/0020418 A1 | 1/2011 | Bosley, Jr. |
| 2011/0038921 A1 | 2/2011 | Wen et al. |
| 2011/0054520 A1 | 3/2011 | Deal et al. |
| 2011/0060362 A1 | 3/2011 | Patel et al. |
| 2011/0070282 A1 | 3/2011 | Nugent et al. |
| 2011/0070284 A1 | 3/2011 | Depaula et al. |
| 2011/0098799 A1 | 4/2011 | Treacy et al. |
| 2011/0104279 A1 | 5/2011 | Marraccini et al. |
| 2011/0135703 A1 | 6/2011 | Shipp |
| 2011/0150918 A1 | 6/2011 | Foster et al. |
| 2011/0166673 A1 | 7/2011 | Patel et al. |
| 2011/0171285 A1 | 7/2011 | Hook et al. |
| 2011/0182963 A1 | 7/2011 | McKay |
| 2011/0190679 A1 | 8/2011 | Humes et al. |
| 2011/0245905 A1 | 10/2011 | Weber et al. |
| 2011/0264190 A1 | 10/2011 | McClain et al. |
| 2011/0264236 A1 | 10/2011 | Bassett et al. |
| 2011/0293666 A1 | 12/2011 | Wang et al. |
| 2011/0305745 A1 | 12/2011 | Gurtner et al. |
| 2012/0034191 A1 | 2/2012 | Matheny |
| 2012/0052124 A1 | 3/2012 | Kaplan et al. |
| 2012/0100225 A1 | 4/2012 | McKay |
| 2012/0135045 A1 | 5/2012 | Nixon et al. |
| 2012/0156164 A1 | 6/2012 | Park et al. |
| 2012/0156255 A1 | 6/2012 | Singh et al. |
| 2012/0171769 A1 | 7/2012 | McGonigle et al. |
| 2012/0209403 A1 | 8/2012 | Morrison et al. |
| 2012/0258174 A1 | 10/2012 | Prior |
| 2012/0282228 A1 | 11/2012 | Bhasin |
| 2012/0282320 A1 | 11/2012 | Scherr |
| 2013/0005829 A1 | 1/2013 | Jamiolkowski et al. |
| 2013/0028984 A1 | 1/2013 | Xu et al. |
| 2013/0052254 A1 | 2/2013 | Arinzeh et al. |
| 2013/0052712 A1 | 2/2013 | Cha et al. |
| 2013/0053665 A1 | 2/2013 | Hughes et al. |
| 2013/0071447 A1 | 3/2013 | Farrell et al. |
| 2013/0079811 A1 | 3/2013 | Agnew et al. |
| 2013/0084320 A1 | 4/2013 | Story et al. |
| 2013/0105348 A1 | 5/2013 | Koob |
| 2013/0110254 A1 | 5/2013 | Osborne |
| 2013/0123920 A1 | 5/2013 | Sun et al. |
| 2013/0131621 A1 | 5/2013 | Van Holten et al. |
| 2013/0144356 A1 | 6/2013 | Horn et al. |
| 2013/0150883 A1 | 6/2013 | Fette et al. |
| 2013/0175729 A1 | 7/2013 | Hassingboe et al. |
| 2013/0183352 A1 | 7/2013 | Xie |
| 2013/0197660 A1 | 8/2013 | Bollati et al. |
| 2013/0202563 A1 | 8/2013 | Badylak et al. |
| 2013/0209571 A1 | 8/2013 | Du et al. |
| 2013/0211249 A1 | 8/2013 | Barnett et al. |
| 2013/0211543 A1 | 8/2013 | Chen et al. |
| 2013/0218201 A1 | 8/2013 | Obermiller et al. |
| 2013/0230601 A1 | 9/2013 | Itskovitz-Eldor et al. |
| 2013/0237816 A1 | 9/2013 | Armstrong |
| 2013/0243738 A1 | 9/2013 | Griffiths et al. |
| 2013/0245528 A1 | 9/2013 | Harrell |
| 2013/0253663 A1 | 9/2013 | Amoroso et al. |
| 2013/0259902 A1 | 10/2013 | Fan et al. |
| 2013/0280223 A1 | 10/2013 | Owens et al. |
| 2013/0280303 A1 | 10/2013 | Drapeau et al. |
| 2013/0280801 A1 | 10/2013 | Sun |
| 2013/0288375 A1 | 10/2013 | Zhang et al. |
| 2013/0304119 A1 | 11/2013 | Armstrong et al. |
| 2013/0304229 A1 | 11/2013 | Biris |
| 2013/0309295 A1 | 11/2013 | Gatenholm |
| 2013/0316454 A1 | 11/2013 | Lu et al. |
| 2013/0330417 A1 | 12/2013 | Dong et al. |
| 2014/0030315 A1 | 1/2014 | Johnson |
| 2014/0065121 A1 | 3/2014 | Suggs et al. |
| 2014/0067046 A1 | 3/2014 | Perry et al. |
| 2014/0088339 A1 | 3/2014 | Matheny |
| 2014/0094671 A1 | 4/2014 | Boock et al. |
| 2014/0099256 A1 | 4/2014 | Zheng et al. |
| 2014/0099352 A1 | 4/2014 | Matheny |
| 2014/0100648 A1 | 4/2014 | Matheny |
| 2014/0107555 A1 | 4/2014 | Patel |
| 2014/0113967 A1 | 4/2014 | Neas et al. |
| 2014/0121750 A1 | 5/2014 | Hadley et al. |
| 2014/0141054 A1 | 5/2014 | Bosley, Jr. et al. |
| 2014/0142200 A1 | 5/2014 | Duan et al. |
| 2014/0148914 A1 | 5/2014 | Mohan et al. |
| 2014/0170117 A1 | 6/2014 | Ling et al. |
| 2014/0178450 A1 | 6/2014 | Christman |
| 2014/0180399 A1 | 6/2014 | Alavi et al. |
| 2014/0188250 A1 | 7/2014 | Fearnot et al. |
| 2014/0205648 A1 | 7/2014 | Maccecchini |
| 2014/0343673 A1 | 11/2014 | Matheny |
| 2014/0345118 A1 | 11/2014 | Rolle et al. |

FOREIGN PATENT DOCUMENTS

| | | |
|---|---|---|
| EP | 1261365 B1 | 3/2001 |
| EP | 1610728 B1 | 4/2004 |
| EP | 0792125 B1 | 11/2004 |
| EP | 0741785 B2 | 8/2005 |
| EP | 1674116 A2 | 6/2006 |
| EP | 1056486 B1 | 10/2006 |
| EP | 0769961 B1 | 11/2006 |
| EP | 1203075 B1 | 9/2007 |
| EP | 1216296 B1 | 4/2009 |
| EP | 1706070 B1 | 2/2011 |
| EP | 1691720 B1 | 6/2011 |
| EP | 2478872 A1 | 7/2012 |
| EP | 1404390 B1 | 8/2012 |
| EP | 1942960 B1 | 8/2012 |
| EP | 1612265 B1 | 1/2013 |
| EP | 2043531 B1 | 1/2013 |
| EP | 2561831 A1 | 2/2013 |
| EP | 2596762 A1 | 5/2013 |
| EP | 2606917 A1 | 6/2013 |
| EP | 2634251 A1 | 9/2013 |
| EP | 2644620 A1 | 10/2013 |
| EP | 2644692 A1 | 10/2013 |
| EP | 2187983 B1 | 4/2014 |
| EP | 1501444 B1 | 5/2014 |
| EP | 2324867 B1 | 6/2014 |
| EP | 2117611 B1 | 7/2014 |
| WO | WO 96/39203 A1 | 12/1996 |
| WO | WO 96/39430 A1 | 12/1996 |
| WO | WO 97/30662 A1 | 8/1997 |
| WO | WO 00/47130 A1 | 8/2000 |
| WO | WO 00/53795 A1 | 9/2000 |
| WO | WO 00/56375 A2 | 9/2000 |
| WO | WO 01/012106 A1 | 2/2001 |
| WO | WO 01/054619 A1 | 8/2001 |
| WO | WO 01/066472 A1 | 9/2001 |
| WO | WO 03/007795 A2 | 1/2003 |
| WO | WO 03/030956 A2 | 4/2003 |
| WO | WO 03/092471 A2 | 11/2003 |
| WO | WO 2004/073616 A2 | 9/2004 |
| WO | WO 2004/098671 A2 | 11/2004 |
| WO | WO 2005/034789 A1 | 4/2005 |
| WO | WO 2005/034852 A2 | 4/2005 |
| WO | WO 2005/042046 A1 | 5/2005 |
| WO | WO 2005/042048 A2 | 5/2005 |
| WO | WO 2005/046327 A1 | 5/2005 |
| WO | WO 2005/046445 A2 | 5/2005 |
| WO | WO 2005/062868 A2 | 7/2005 |
| WO | WO 2005/073365 A1 | 8/2005 |
| WO | WO 2005/079388 A2 | 9/2005 |
| WO | WO 2005/079675 A2 | 9/2005 |
| WO | WO 2005/096954 A2 | 10/2005 |
| WO | WO 2005/096993 A1 | 10/2005 |
| WO | WO 2005/097219 A2 | 10/2005 |
| WO | WO 2005/112821 A2 | 12/2005 |
| WO | WO 2005/121316 A1 | 12/2005 |
| WO | WO 2006/026325 A2 | 3/2006 |
| WO | WO 2006/050091 A2 | 5/2006 |
| WO | WO 2006/056984 A2 | 6/2006 |
| WO | WO 2006/060546 A2 | 6/2006 |
| WO | WO 2006/066327 A1 | 6/2006 |
| WO | WO 2006/121887 A2 | 11/2006 |
| WO | WO 2006/124021 A1 | 11/2006 |

(56) References Cited

FOREIGN PATENT DOCUMENTS

| | | |
|---|---|---|
| WO | WO 2007/011443 A2 | 1/2007 |
| WO | WO 2007/035791 A2 | 3/2007 |
| WO | WO 2007/059497 A2 | 5/2007 |
| WO | WO 2007/084609 A2 | 7/2007 |
| WO | WO 2007/090150 A2 | 8/2007 |
| WO | WO 2007/090155 A1 | 8/2007 |
| WO | WO 2007/098484 A2 | 8/2007 |
| WO | WO 2007/120840 A2 | 10/2007 |
| WO | WO 2007/144644 A2 | 12/2007 |
| WO | WO 2007/149989 A2 | 12/2007 |
| WO | WO 2008/003320 A2 | 1/2008 |
| WO | WO 2008/032928 A2 | 3/2008 |
| WO | WO 2008/045638 A2 | 4/2008 |
| WO | WO 2008/075206 A2 | 6/2008 |
| WO | WO 2008/100967 A2 | 8/2008 |
| WO | WO 2008/105791 A2 | 9/2008 |
| WO | WO 2008/122595 A2 | 10/2008 |
| WO | WO 2008/124361 A2 | 10/2008 |
| WO | WO 2008/134541 A2 | 11/2008 |
| WO | WO 2008/144476 A1 | 11/2008 |
| WO | WO 2008/151040 A2 | 12/2008 |
| WO | WO 2009/020650 A2 | 2/2009 |
| WO | WO 2009/025970 A1 | 2/2009 |
| WO | WO 2009/027814 A1 | 3/2009 |
| WO | WO 2009/035779 A1 | 3/2009 |
| WO | WO 2009/042514 A1 | 4/2009 |
| WO | WO 2009/042768 A1 | 4/2009 |
| WO | WO 2009/045824 A2 | 4/2009 |
| WO | WO 2009/048314 A1 | 4/2009 |
| WO | WO 2009/064839 A1 | 5/2009 |
| WO | WO 2009/111306 A2 | 9/2009 |
| WO | WO 2010/019753 A2 | 2/2010 |
| WO | WO 2010/027898 A1 | 3/2010 |
| WO | WO 2010/059389 A2 | 5/2010 |
| WO | WO 2010/065843 A2 | 6/2010 |
| WO | WO 2010/072417 A9 | 7/2010 |
| WO | WO 2010/078478 A1 | 7/2010 |
| WO | WO 2010/086856 A2 | 8/2010 |
| WO | WO 2010/088678 A2 | 8/2010 |
| WO | WO 2010/088735 A1 | 8/2010 |
| WO | WO 2010/096458 A1 | 8/2010 |
| WO | WO 2010/099463 A2 | 9/2010 |
| WO | WO 2011/042794 A2 | 4/2011 |
| WO | WO 2011/113507 A2 | 9/2011 |
| WO | WO 2011/150055 A2 | 12/2011 |
| WO | WO 2011/150482 A1 | 12/2011 |
| WO | WO 2011/154687 A1 | 12/2011 |
| WO | WO 2011/161180 A1 | 12/2011 |
| WO | WO 2012/003377 A2 | 1/2012 |
| WO | WO 2012/018680 A1 | 2/2012 |
| WO | WO 2012/034110 A3 | 3/2012 |
| WO | WO 2012/050836 A1 | 4/2012 |
| WO | WO 2012/094611 A1 | 7/2012 |
| WO | WO-2012/099703 A1 | 7/2012 |
| WO | WO 2012/124353 A1 | 9/2012 |
| WO | WO 2012/145756 A1 | 10/2012 |
| WO | WO 2012/158169 A1 | 11/2012 |
| WO | WO 2012/162753 A1 | 12/2012 |
| WO | WO 2012/170538 A2 | 12/2012 |
| WO | WO 2013/174234 A2 | 12/2012 |
| WO | WO 2013/003229 A1 | 1/2013 |
| WO | WO 2013/010169 A1 | 1/2013 |
| WO | WO 2013/045689 A1 | 4/2013 |
| WO | WO 2013/059745 A1 | 4/2013 |
| WO | WO 2013/086149 A1 | 6/2013 |
| WO | WO 2013/096255 A2 | 6/2013 |
| WO | WO 2013/119551 A1 | 8/2013 |
| WO | WO 2013/134009 A1 | 9/2013 |
| WO | WO 2013/188449 A1 | 12/2013 |
| WO | WO 2014/026052 A1 | 2/2014 |
| WO | WO 2014/040026 A2 | 3/2014 |
| WO | WO 2014/047246 A1 | 3/2014 |
| WO | WO 2014/047287 A1 | 3/2014 |
| WO | WO 2014/058587 A1 | 4/2014 |
| WO | WO 2014/058589 A1 | 4/2014 |
| WO | WO 2014/066297 A1 | 5/2014 |
| WO | WO 2014/066724 A1 | 5/2014 |
| WO | WO 2014/099323 A1 | 6/2014 |

OTHER PUBLICATIONS

Chun, S. et al., "Identification and Characterization of Bioactive Factors in Bladder Submucosa Matrix," *Biomaterials*, vol. 28, pp. 4251-4256 (2007).
Crapo, P. et al., "An Overview of Tissue and Whole Organ Decellularization Processes," *Biomaterials*, vol. 32, No. 12, pp. 3233-3243 (2011).
De Mello, M. F. V. et al., Distribution of Collagen Types I, III, and IV in Gastric Tissue of Marmosets (*Callithrix* spp., Callitrichidae: Primates), *Pesq. Vet. Bras.*, vol. 30, No. 4, pp. 317-320 (2010).
Gibson, M. et al., "Tissue Extracellular Matrix Nanoparticle Presentation in Electrospun Nanofibers," *Biomed Research International*, vol. 2014, Article ID 469120, pp. 1-13 (2014).
Gumati, M. K. et al., "Extracellular Matrix of Different Composition Supports the Various Splenic Compartments of Guinea Fowl (*Numida meleagris*)," *Cell Tissue Res.*, vol. 312, pp. 333-343 (2003).
Hodde, J.P. et al., "Bioactive FGF-2 in Sterilized Extracellular Matrix," *Wounds*, vol. 13, No. 5, pp. 195-201 (2001) (abstract only).
Hodde, J.P. et al., "Vascular Endothelial Growth Factor in Porcine-Derived Extracellular Matrix," *Endothelium*, vol. 8, No. 1, pp. 11-24 (2001).
Lokmic, Z. et al., "The Extracellular Matrix of the Spleen as a Potential Organizer of Immune Cell Compartments," *Seminars in Immunology*, vol. 20, No. 1, pp. 4-13 (2008).
Mandlewala, R. et al., "Adsorption-Desorption Study of BSA Conjugated Silver Nanoparticles on Collagen Immobilized Substrates," retrieved from http://www.coassymposium.com/sampleabstracts/richa_mandlewala8246.pdf . . . .
McDevitt, C.A. et al., "Transforming Growth Factor-β1 in a Sterilized Tissue Derived from the Pig Small Intestine Submucosa," *J. Biomed. Res.*, vol. 67A, pp. 637-640 (2003).
Mohiti-Asli, M. et al., "Novel, Silver-Ion-Releasing Nanofibrous Scaffolds Exhibit Excellent Antibacterial Efficacy Without the Use of Silver Nanoparticles," *Acta Biomater.*, vol. 10, pp. 2096-2104 (2014).
Nichols, J.E. et al., "Production and Assessment of Decellularized Pig and Human Lung Scaffolds," *Tissue Eng.; Part A*, vol. 19, Nos. 17-18, pp. 2045-2062 (2013).
O'Neill, J. et al., "Decellularization of Human and Porcine Lung Tissues for Pulmonary Tissue Engineering," *Ann. Thorac. Surg.*, vol. 96, No. 3, pp. 1046-1056 (2013).
Parsons, D. et al., "Silver Antimicrobial Dressings in Wound Management: A Comparison of Antibacterial, Physical, and Chemical Characteristics," *Wounds*, vol. 17, No. 8, pp. 222-232 (2005).
Percival et al., "Bacterial resistance to silver in wound care," *Journal of Hospital Infection*, vol. 60, pp. 1-7 (2005).
Petersen T. et al., "In Vitro Development of Engineered Lung Tissue," Dissertation, Dept. of Biomedical Engineering, Duke University (2009) (283 pages).
Petersen, T. et al., "Matrix Composition and Mechanics of Decellularized Lung Scaffolds", *Cells Tissues Organs*, vol. 195, pp. 222-231 (2012).
Pouliot, R. et al., "Lung Tissue Derived Extracellular Matrix Hydrogels Promote Mouse Mesenchymal Stem Cell Proliferation, Attachment and Differentiation," American Journal of Respiratory and Critical Care Medicine, Meeting Abstracts, vol. 187, pp. A4991-A4991 (2013), available at http://www.atsjournals.org/doi/abs/10.1164/ajrccm-conference.2013.187.1_MeetingAbstracts.A4991.
Wang, L. et al., "Decellularized Musculofascial Extracellular Matrix for Tissue Engineering," *Biomaterials*, vol. 11, pp. 2641-2654 (2013) (abstract only).
Zhou, H.Y. et al., "Improving the Antibacterial Property of Porcine Small Intestinal Submucosa by Nano-Silver Supplementation," *Ann Surg.*, vol. 253, No. 5, pp. 1033-1041 (2011).
International Search Report for PCT/US2015/065436 dated Jun. 27, 2016 (7 pages).

TISSUE-BASED COMPOSITIONS AND METHODS OF USE THEREOF

CROSS-REFERENCE TO RELATED APPLICATIONS

This application is a continuation of U.S. application Ser. No. 14/963,571, filed on Dec. 9, 2015, which is a continuation of U.S. application Ser. No. 14/582,288, filed on Dec. 24, 2014, issued as U.S. Pat. No. 9,238,090, each of which is incorporated by reference herein in its entirety.

TECHNICAL FIELD

The present disclosure generally relates to compositions comprising extracellular matrix (ECM) material and methods of use thereof.

BACKGROUND

Biomaterials have been used in a variety of medical applications as alternative to, or in conjunction with, conventional materials in order to assist with healing, tissue repair, and other forms of medical treatment. Such biomaterials include ECM, a complex structural material found within tissues that surround and support cells. The ECM is generally made up of three major classes of biomolecules: structural proteins such as collagen and elastin; other proteins such as laminin, fibronectin, and various growth factors; and proteoglycans. ECM is derived from collageneous tissue and processed for application at the site of bodily injury. While ECM materials can be used for certain medical applications, current ECM materials often fail to provide sufficient structural integrity and bioactivity.

SUMMARY

The present disclosure includes a composition comprising a first extracellular matrix material derived from spleen tissue; and a second extracellular matrix material derived from at least one mammalian tissue chosen from lung tissue, gall bladder tissue, bone marrow tissue, pancreatic tissue, or liver tissue, the second extracellular matrix material being at least partially integrated into the first extracellular matrix material, wherein at least a portion of the composition is in particulate form, and wherein the composition is configured for administration to a patient. Embodiments of the present disclosure may include one or more of the following features: the first and/or second extracellular matrix material may be in particulate form; the second extracellular matrix material may be derived from lung tissue; one of the first extracellular matrix material or the second extracellular matrix material may be in particulate form, and the other of the first extracellular matrix and the second extracellular matrix may be in gel form; one of the first extracellular matrix material or the second extracellular matrix material may be in particulate form, and the other of the first extracellular matrix material or the second extracellular matrix material may be in sheet form; the composition may be configured for application to native tissue of the patient for repairing the native tissue; the composition may have a rod-like shape or a tubular shape; at least a portion of the second extracellular matrix material may be in particulate form, such that the second extracellular matrix particulate material may be incorporated into the first extracellular matrix material, wherein the second extracellular matrix material may be derived from lung tissue; the composition may include at least two layers, wherein at least one of the layers comprises the second extracellular matrix particulate material integrated into the first extracellular matrix material; the composition may further comprise at least one antimicrobial agent such as ionic silver; the first extracellular matrix material may have a concentration of at least one growth factor higher than a concentration of the at least one growth factor of the second extracellular matrix material; and/or the at least one growth factor may be chosen from vascular endothelial growth factor (VEGF), fibroblast growth factor (FGF), platelet-derived growth factor (PDGF), insulin-like growth factor (IGF), or epidermal growth factor (EGF).

The present disclosure further includes a composition comprising a first extracellular matrix material derived from spleen tissue, and a second extracellular matrix material derived from at least one mammalian tissue chosen from lung tissue, gall bladder tissue, bone marrow tissue, pancreatic tissue, or liver tissue, the second extracellular matrix material being at least partially integrated into the first extracellular matrix material, wherein the first extracellular matrix material has a higher growth factor content than the second extracellular matrix material, and the second extracellular matrix material is at least partially integrated into the first extracellular matrix material, wherein the first extracellular matrix material is in a form different from a form of the second extracellular matrix material, and wherein the composition is configured for application to native tissue of a patient for repairing the native tissue. Embodiments of the present disclosure may include one or more of the following features: one of the first extracellular matrix material or the second extracellular matrix material may be in particulate form, and the other of the first extracellular matrix material and the second extracellular matrix material may be in gel form; the first extracellular matrix material may have a higher concentration of vascular endothelial growth factor (VEGF) than the second extracellular matrix material, and the second extracellular matrix material may have a higher concentration of elastin than the first extracellular matrix material; the first extracellular matrix material may have a higher concentration of platelet-derived growth factor (PDGF) than the second extracellular matrix material, and the second extracellular matrix material may have a higher concentration of fibroblast growth factor (FGF) than the first extracellular matrix material; and/or the first extracellular matrix material may have a higher concentration of epidermal growth factor (EGF) than the second extracellular matrix material, and the second extracellular matrix material may have a higher concentration of vascular endothelial growth factor (VEGF) than the first extracellular matrix material.

The present disclosure further includes a composition comprising a first extracellular matrix material derived from spleen tissue, and a second extracellular matrix material derived from lung tissue, wherein the composition includes at least two layers, at least one of the layers comprising the second extracellular matrix material at least partially integrated into the first extracellular matrix material, and wherein the composition is configured for application to native tissue of a patient for repairing the native tissue. Embodiments of the present disclosure may include one or more of the following features: the first extracellular matrix material may be derived from a reticular portion of the spleen tissue, such that the first extracellular matrix material may be at least partially porous; the first extracellular matrix material also may be derived from an outer membrane of the spleen tissue, such that the first extracellular matrix material may have a sheet-like portion and a porous portion, the second extracellular matrix material being integrated into the porous portion of the first extracellular matrix material; the second extracellular matrix material may be in particulate form, gel form, or liquid form; the composition may have a rod-like shape configured for implantation into the patient; the composition may further comprise a third extracellular matrix material, wherein at least one of the layers of the composition may comprise the third extracellular matrix material in sheet form, wherein the third extracellular matrix material may be derived from lung tissue or spleen tissue; and/or the composition may have a rod-like shape or a tubular shape.

The present disclosure further includes a composition comprising a first extracellular matrix material derived from spleen tissue, and a second extracellular matrix material derived from lung tissue, the second extracellular matrix material being in particulate form, gel form, or liquid form, wherein the first extracellular matrix material is in a form different from the form of the second extracellular matrix material, and wherein the composition is configured for application to native tissue of a patient for repairing the native tissue. In some embodiments, at least a portion of the first extracellular matrix material may be in sheet form; and/or the first extracellular matrix material may be derived from a reticular portion of the spleen tissue and an outer membrane of the spleen tissue, such that the first extracellular matrix material may have a sheet-like portion and a porous portion, wherein the second extracellular matrix material may be integrated into the porous portion of the first extracellular matrix material.

BRIEF DESCRIPTION OF THE FIGURES

The accompanying drawings, which are incorporated in and constitute a part of this specification, illustrate various exemplary embodiments and together with the description, serve to explain the principles of the disclosed embodiments. Any features of an embodiment described herein (e.g., composition, medical device, method of treatment, etc.) may be combined with any other embodiment, and are encompassed by the present disclosure.

FIGS. 3A-3C show exemplary compositions according to some embodiments of the present disclosure, wherein FIGS. 3B and 3C show different cross-sectional views of a composition as shown in FIG. 3A.

DETAILED DESCRIPTION

Figure 1:
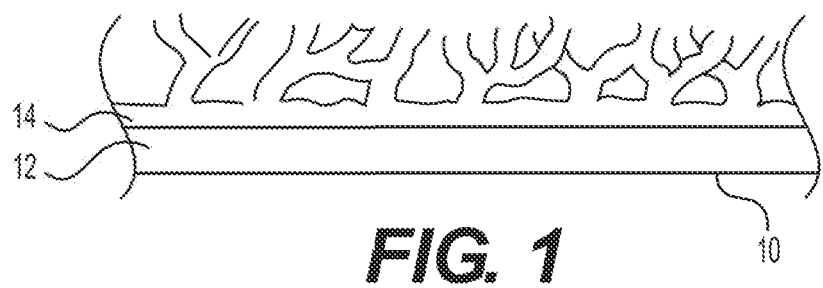
FIG. 1 shows an exemplary composition, in accordance with one or more embodiments of the present disclosure.

The singular forms "a," "an," and "the" include plural reference unless the context dictates otherwise.

The terms "approximately" and "about" refer to being nearly the same as a referenced number or value. As used herein, the terms "approximately" and "about" generally should be understood to encompass ±10% of a specified amount or value.

As used herein, the term "therapeutically-effective amount" relates to an amount of a substance (e.g., an agent, compound, material, etc.) that leads to the desired therapeutic effect(s), and the term "pharmaceutically-effective amount" relates to an amount of a substance (e.g., an agent compound, material, etc.) that leads to the desired pharmacological effect(s). While individual patient needs may vary, determination of optimal ranges for effective amounts of the substances described herein (e.g., ECM materials, growth factors, structural proteins, therapeutic agents, pharmaceutical agents, antimicrobial agents, etc.) is within the skill of the art. For example, suitable amounts or dosages of the substances herein may be selected in accordance with a variety of factors, including the type, age, weight, sex, diet, medical condition, and/or medical history of the patient.

Wound healing and tissue regeneration is a complex multi-stage process within the body. Various and multiple components are involved in different stages. Injured or damaged tissue requires multiple components, e.g., structural proteins and signaling factors, to complete healing at the site of injury. Many of these components have been identified in ECM materials, including fibrous proteins such as different collagen types, elastin, fibronectin, and laminin. ECM also may comprise glycosaminoglycans (GAGs) such as heparin sulfate, and various growth factors. During tissue healing/repair/regeneration, these components play various roles, including, but not limited to, up-regulating and/or down-regulating different stages of the healing process. Rather than one single biomolecule, a number of different components work together to facilitate healing and repair at each stage. Several types of signaling factors are often needed for a specific stage of the healing process to occur. For example, a growth factor may signal a stem cell from the host to migrate to the site of injury. The host cell may need a substrate or structural protein (e.g., a specific collagen type, laminin, or elastin) for attachment or binding to the site, and a different growth factor for signaling in order to differentiate into site-specific tissue.

The present disclosure may address one or more of these challenges, e.g., by combining structural proteins and growth factors or other signaling or structural molecules from different types and/or sources of tissue in order to facilitate tissue repair at a specific injury site.

Types of Materials

The present disclosure includes compositions comprising ECM materials or other collagen-based materials for promoting tissue repair, augmentation, and/or regeneration. For example, the ECM materials may serve as a support structure and/or provide signaling factors to facilitate tissue growth. Materials suitable for the present disclosure may be derived from any mammalian source tissue comprising ECM or other collagen-based materials, including, but not limited to, tissues of the spleen, kidney, liver, lung, pancreas, gall bladder, stomach, pericardium, lymph node, bone marrow, dermis, placenta, amniotic sac, dura mater, and any combinations thereof. ECM source material may be used in whole or in part.

The ECM materials may be obtained from tissue by removing the entirety of the tissue (e.g., an organ) or a portion thereof from the desired mammalian source, and devitalizing the tissue by removing the cellular content of the tissue. The ECM source material may comprise all layers of a type of tissue or an entire organ, for example, or may comprise only one or more portions of tissue such as the submucosa, the basement membrane, a tunica layer, the reticular ECM, or the outer membrane of the source tissue such as the pleura of the lung or the capsule of the kidney.

The ECM materials of the present disclosure may comprise any combination of these different portions or layers of tissue. Examples of types of native tissues suitable for the present disclosure include, but are not limited to, porcine, bovine, ovine, and human tissue. In some embodiments, the composition may comprise one or more non-mammalian tissues such as fish tissue, e.g., fish skin, optionally in combination with one or more mammalian tissues.

In some embodiments, the composition may comprise ECM materials derived from two or more different tissue sources and/or two or more different native tissues. For example, the tissue sources can be from the same species (e.g., ECM materials derived from different types of tissues of the same mammal), from different species (e.g., ECM materials derived from the same type of tissue of different types of mammals), or both (e.g., ECM materials derived from different types of tissues of different types of mammals). In some embodiments, the composition may comprise spleen ECM and/or lung ECM from the same species or different species. For example, embodiments of the present disclosure may include, but are not limited to, compositions comprising the following:

Porcine spleen ECM and porcine lung ECM
Bovine spleen ECM and porcine spleen ECM
Bovine lung ECM and porcine spleen ECM
Bovine lung ECM, bovine spleen ECM, and porcine spleen ECM The composition may comprise spleen ECM and at least one other ECM material chosen from lung, gall bladder, bone marrow, pancreas, or liver. For example, the composition may comprise spleen ECM, lung ECM, and/or at least one other ECM material. Other combinations of ECM materials will be apparent in view of the disclosure herein.

In addition to ECM materials, the compositions may comprise one or more other compounds or materials, such as resorbable synthetic or natural materials, non-resorbable synthetic or natural materials, polymers, metals, bone material, allograft tissues or bones, antimicrobial agents, therapeutic agents, pharmaceutical agents (drugs), or any combination thereof. In some embodiments, the composition may be formulated for administration to patient and/or configured as a medical device or component thereof for application or implantation into a patient.

In some embodiments, for example, the composition may comprise spleen and lung ECM, optionally in combination with one or more other types of ECM materials and/or one or more non-ECM components. For example, a composition of spleen and lung ECM may comprise one or more other types of ECM materials including, but not limited to, heart membrane ECM, pericardium ECM, pancreas ECM, fascia ECM, dura mater ECM, omentum ECM, gall bladder ECM, amniotic sac ECM, kidney capsule ECM, liver ECM, or bone marrow ECM. In at least one embodiment, the composition may comprise spleen ECM, lung ECM, and one or more non-ECM components chosen from polymers, hydrogels, or hyaluronic acid.

Preparation/Treatment of ECM Materials

Methods of preparing devitalized or acellular tissue may include physical, chemical, and/or biological processes. For example, mammalian tissue may be harvested and subjected to a physical cleaning process to remove fat, muscle, and other cellular material extraneous to the ECM. Such physical processes may include machine-based mechanical actions and/or force applied manually. In addition or alternatively, the tissue may be subjected to chemical and/or biological processes to rupture cells and remove cellular material. For example, the tissue may be exposed to one or more chemical or biological agents including, but not limited to, an acid (e.g., HCl, acetic acid, peracetic acid), a base (e.g., NaOH), a chelating agent (e.g., ethylenediaminetetraacetic acid (EDTA), ethylene glycol tetraacetic acid (EGTA)), a detergent (e.g., sodium dodecyl sulfate, Triton-X, CHAPS), and/or an enzyme (e.g., nuclease, trypsin, collagenase). Further examples of decellularization processes include high pressure homogenization, and hypotonic or hypertonic washes for rupturing cells in ECM materials and washing away the cellular material. The ECM materials may be dried, e.g., at ambient temperature and pressure or in vacuum, frozen, and/or stored prior to use. Methods of drying ECM materials suitable for the present disclosure include desiccation chambers, controlled humidity chambers, forced air flow drying, and lyophilization (freeze-drying).

The process(es) involved in decellularization may be selected to preserve one or more biological materials of interest. Decellularization may be different for each type of tissue, based on the desired components and/or structure to be retained, and the treatment suitable for retaining those components and/or structure. Embodiments of the present disclosure may comprise ECM materials derived from at least two different types of tissue, each tissue subjected to one or more decellularization processes selected to retain particular characteristics of the tissue.

In some embodiments, for example, lung tissue may be decellularized with detergents such as sodium dodecyl sulfate or Triton-X to retain as much elastin from the material as possible while sacrificing some of the growth factor content. In addition to elasticity, other benefits to using lung ECM may include liquid impermeability, e.g., to prevent fluid within the composition from leaking out and/or to prevent bodily fluids from permeating into or through the composition. In addition, lung ECM may be processed in such a way to provide one relatively smooth surface that discourages the attachment of patient tissue to the composition, while the opposite surface may have a more porous structure that facilitates cell attachment. Lung ECM also may be particularly suitable for applications that require materials with stretch and/or rebound properties, such as bladder augmentation, vascular graft, or vascular patch applications. Further, lung ECM may be relatively thin (e.g., derived from lung tissue that is relatively thin in comparison to other types of tissues), which may provide for a beneficial strength-to-weight ratio in comparison to other types of ECM materials.

Spleen tissue, on the other hand, may be decellularized to preserve as much growth factor content as possible by treating the tissue with a more gentle acid wash, such as peracetic acid having a concentration ranging from about 0.01% to about 5.00%, such as about 0.1%. The decellularized spleen tissue may be rinsed with buffered saline and/or water to retain a maximum amount of growth factor. The reticular structure of spleen ECM may provide interstitial spaces suitable for accommodating other types of ECM materials (e.g., in particulate, gel, or paste form), biomolecules, antimicrobial agents (see discussion below), and/or pharmaceutical agents. Further, the reticular structure of spleen ECM, e.g., in combination with the growth factors retained in the matrix, may foster and support the growth of new cells within the matrix to promote tissue grafting. For example, spleen ECM may be particularly suitable for hemostasis and reconstructive surgery applications.

In some embodiments, spleen tissue may be processed to generate ECM material comprising only a portion, e.g., a fibrous portion, of the native tissue. For example, only the outer membrane of the spleen may be used to generate spleen ECM in sheet form. Further, for example, only the reticular ECM of the spleen may be used to generate an open structure fibrous ECM sheet. In yet another example, both the outer membrane and the reticular ECM component of the spleen may be used such that they remain intact, e.g., to generate an ECM material having a relatively more dense, sheet-like structure on one side with a relatively more porous or fibrous sponge-like structure on the other side.

During processing, ECM materials may shrink when dried and then expand to some degree when they are rehydrated, e.g., as they absorb fluid. For example, an ECM material in sheet form may be about 200 µm thick when dry, and may increase to a thickness from about 300 µm to about 500 µm when rehydrated. The natural fibrous architecture of tissues such as the spleen may allow for more expansion, e.g., since the naturally-occurring reticular ECM component generally has "dead space" to allow for compression and expansion when rehydrated. ECM materials may be processed to adjust for compression/rehydration/expansion characteristics of the native tissue.

In some embodiments, the composition may comprise a plurality of ECM materials, wherein at least one of the ECM materials comprises a different variety of components and/or a different amount or concentration of a given component than another ECM material in the composition. Further, in some embodiments, the composition may comprise two or more ECM materials that comprise some or all of the same variety of components, but different amounts or concentrations of those components. In some embodiments, the composition may comprise two or more ECM materials that comprise some or all of the same variety of components and/or substantially the same amount or concentration (or a similar amount or concentration) of a given component as another ECM material in the composition. These components may include proteins, glycoproteins, glycosaminoglycans, proteoglycans, cytokines, and/or growth factors. For example, the composition may comprise ECM materials having substantially the same, similar, or different amounts of one or more of the following components: collagen, elastin, fibronectin, laminin, heparin sulfate, fibroblast growth factor (FGF), vascular endothelial growth factor (VEGF), transforming growth factors alpha (TGF-α), transforming growth factors beta (TGF-β), platelet-derived growth factor (PDGF), epidermal growth factor (EGF), keratinocyte growth factor (KGF), bone morphogenetic proteins (BMPs), epidermal growth factor (EGF), brain-derived neurotrophic factor (BDNF), growth differentiation factor-9 (GDF9), hepatocyte growth factor (HGF), insulin-like growth factor (IGF), nerve growth factor (NGF), skeletal growth factor (SGF), osteoblast-derived growth factor (BDGF), cytokine growth factors (CGF), stem cell derived factor (SDF), stem cell factor (SCF), placental growth factor (PGF), and/or interleukins of any type and within any family (e.g., IL-1, IL-2, etc.).

Biological components may be detected and quantified in the ECM materials and/or in the native tissues via enzyme-linked immunosorbent assay (ELISA), or any other suitable technique. Table 1 lists growth factors measured in different porcine ECM materials: small intestine submucosa (SIS), urinary bladder submucosa (UBS), stomach submucosa (SS), spleen, and lung. The SS, spleen, and lung measurements are described in Example 1.

TABLE 1

Growth factors in porcine ECM materials.

| | SIS (ng/g)[1] | UBS (pg/g)[2] | SS (ng/mg)[3,4] | Spleen (ng/mg)[3,5] | Lung (ng/mg)[3,6] |
|---|---|---|---|---|---|
| VEGF | 0.77 | 104.6 ± 25.4 | 10.5 ± 1.6 | 8.7 ± 1.2 | 11.4 ± 2.7 |
| FGF | 97.9 ± 11.7 | 4.0427 ± 0.0075 | 0.6 | 1.0 | 1.1 |
| TGF-β | 768.1 ± 182.1 | 8.8490 ± 0.001 | — | — | — |
| PDGF | — | 285.62 ± 4.54 | 6.1 | 6.5 | 6.1 |
| IGF | — | 6.9 ± 3.4 | 0.4 | 1.6 | 2.8 |
| EGF | — | 0.99 ± 0.15 | 3.5 ± 2.4 | 5.2 ± 0.6 | 5.0 ± 1.6 |
| KGF | — | 158.8 ± 45.4 | — | — | — |

[1]Hodde et al., *Endothelium*, vol. 8, pp. 11-24 (2001); McDevitt et al., *J. Biomed. Mater. Res.*, vol. 67A, pp. 637-640 (2003); Hodde et al., *Wounds*, vol. 13, pp. 195-201 (2001).
[2]Chun et al., *Biomaterials*, vol. 28, pp. 4251-4256 (2007).
[3]Highest value measured of any extraction liquid.
[4]Values (ng/mg) with PBS extraction, VEGF = 8.7 ± 0.4, PDGF = 6.1, EGF = 3.5 ± 2.4; with RIPA buffer extraction, VEGF = 6.3 ± 0.2, IGF = 0.1, EGF = 1.9 ± 0.7; with acetic acid extraction, VEGF = 10.5 ± 1.6, FGF = 0.6, PDGF = 3.4, IGF = 0.4, EGF = 2.2 ± 0.8.
[5]Values (ng/mg) with PBS extraction: VEGF = 8.2 ± 0.1, PDGF = 6.5, IGF = 0.1, EGF = 5.2 ± 0.6; with RIPA buffer extraction: VEGF = 6.6 ± 0.4, IGF = 0.2, EGF = 5.0 ± 0.6; with acetic acid extraction: VEGF = 8.7 ± 1.2, FGF = 1.0, PDGF = 6.4, IGF = 1.6, EGF = 4.1 ± 0.5.
[6]Values (ng/mg) with PBS extraction: VEGF = 3.8 ± 0.2, PDGF = 6.1, IGF = 0.03, EGF = 5.1 ± 1.6; with RIPA buffer extraction: VEGF = 3.2 ± 0.1, IGF = 0.1, EGF = 3.6 ± 0.8; with acetic acid extraction: VEGF = 11.4 ± 2.7, FGF = 1.1, PDGF = 4.9, IGF = 2.8, EGF = 3.5 ± 1.0.

The growth factor content measured may vary according to the type of extraction liquid and/or method used. For example, in some embodiments, the content of different growth factors in stomach submucosa ECM may range from about 6.3±0.2 ng/mg to about 10.5±1.6 ng/mg of VEGF, from about 3.4 ng/mg to about 6.1 ng/mg of PDGF, from about 0.1 ng/mg to about 0.4 ng/mg of IGF, and/or from about 1.9±0.7 ng/mg to about 3.5±2.4 ng/mg of EGF. In some embodiments, the content of different growth factors in spleen ECM may range from about 6.6±0.4 ng/mg to about 8.7±1.2 ng/mg of VEGF, from about 6.4 ng/mg to about 6.5 ng/mg of PDGF, from about 0.1 ng/mg to about 1.6 ng/mg of IGF, and/or from about 4.1±0.5 ng/mg to about 5.2±0.6 ng/mg of EGF. In some embodiments, the content of different growth factors in lung ECM may range from about 3.2±0.1 ng/mg to about 11.4±2.7 ng/mg of VEGF, from about 4.9 ng/mg to about 6.1 ng/mg of PDGF, from about 0.03 ng/mg to about 2.8 ng/mg of IGF, and/or from about 3.5±1.0 ng/mg to about 5.1±1.6 ng/mg of EGF.

Spleen and lung ECM each generally have greater growth factor content than SIS, UBS (or urinary bladder matrix, UBM), and SS ECM. While each of these five types of ECM materials comprises multiple collagen types, lung ECM generally has the greatest quantity of elastin. Elastin may provide better clinical results when used in applications requiring stretch and rebound, such as compliance in a vascular graft or vascular patch application. SIS, UBS/UBM, SS, and lung pleura ECM all naturally occur in sheet form, whereas the spleen can be processed to retain much of the reticular ECM component. The reticular structure provides for a natural three-dimensional ECM with a macroscopic fibrous ECM network. This natural macro-fibrous spleen reticular ECM may be beneficial for a variety of medical applications, such as repair of defects in plastic and reconstructive surgery, use as a layer in a surgical graft such as hernia repair to facilitate better tissue ingrowth, as a hemostasis device, or as a natural scaffold for better incorporation of other ECM or non-ECM components, such as particulates, gels, and polymers.

Compositions according to the present disclosure may comprise the same or different amounts of each ECM material. In some embodiments, the composition may comprise two different ECM materials, e.g., in a ratio ranging from about 50:50 (i.e., 1:1) to about 5:95 (i.e., 1:19). For example, the composition may comprise a 50:50 ratio of two different ECM materials (e.g., spleen ECM and lung ECM), or a ratio of 60:40, 70:30, 80:20, 90:10, 40:60, 30:70, 20:80, 10:90, or any other ratios in between. For example, the composition may comprise lung and spleen tissues in a 1:3 ratio (e.g., about 25% lung ECM and about 75% spleen ECM, or about 25% spleen ECM and about 75% lung ECM). In some embodiments, the composition may comprise more than two different ECM materials, e.g., three, four, five or more ECM materials, in equal or unequal amounts. For example, the composition may comprise three different ECM materials having a ratio of 40:40:20, 30:30:40, or 20:20:60, among other possible ratios. In some embodiments, for example, the composition may comprise about 25% spleen ECM, about 25% lung ECM, and about 50% gall bladder ECM. Any desired ratio may be selected based on the desired final composition.

The ratios of ECM materials in the composition may be chosen based on the individual characteristics of the ECM materials and desired application for the composition. Regenerative medicine applications for which the ratios of ECM materials can be adjusted, e.g., to take advantage of the physical, mechanical, and/or biological characteristics of each ECM material include, but are not limited to, wound dressings, dura repair, fistula plugs, myocardial patches, myocardial injections, heart valve repair, tympanoplasty grafts, nasal septal defect repair, hernia or body wall repair, hemostasis grafts, urology slings, tracheal grafts, esophageal grafts, lung patches, small bowel grafts, staple bolsters, nerve grafts, spinal cord repair, nerve cuff, nerve guide, pelvic floor grafts, amniotic sac patches, cornea repair, cartilage repair, bone repair, tendon/ligament repair, muscle repair, plastic and reconstructive surgery applications, lip augmentation, facial augmentation, nipple reconstruction, bile duct repair, ureter repair, urethra repair, and vascular access graft. By varying the ratio and types of ECM materials applied in a medical application, higher levels of signaling factors and/or other components needed for each specific tissue repair type may be provided.

In wound care applications, for example, a higher ratio of spleen ECM to lung ECM may be desired to utilize a relatively higher EGF content in spleen tissue while also taking advantage of a relatively higher VEGF content in lung tissue. For vascular graft applications, a higher ratio of lung ECM to spleen ECM may be desired to take advantage of higher elastin content and lower gas/liquid permeability of lung tissue, while utilizing a relatively higher PDGF content in spleen tissue. In some embodiments, the composition may comprise a tissue graft composition comprising a plurality of ECM materials, wherein at least two of the ECM materials are derived from different tissue sources and have different growth factor content or protein content.

Forms of Materials

The compositions may comprise ECM materials or collagen-based materials in a variety of different forms, and may be administered to a patient as a formulation (e.g., a liquid for injection or powder for inhalation), or delivered as part of a medical device (e.g., a topical bandage or implantable medical device). For example, the ECM materials or collagen-based materials may be formed into a sheet, rod, tube, three-dimensional construct, mesh, sponge, liquid, gel, hydrogel, emulsion, particles, powder (e.g., fine particles) suspension, paste, putty, dispersion, foam, or any combination thereof, among other possible forms. The composition may comprise a combination of ECM materials or collagen-based materials in different forms, such as sheet and powder, powder and gel, sheet and gel, sponge and liquid, sponge and gel, sheet/powder/gel, sheet/powder/sheet, sheet/gel/sheet, sheet/gel/powder/sheet, sponge/sheet, sponge/gel, sponge/powder, sponge/powder/sheet, sponge/gel/sheet, sponge/powder/gel/sheet, foam/powder, foam/gel, foam/sheet, foam/powder/sheet, and foam/powder/gel/sheet, among other combinations.

In some embodiments, the composition may comprise a multilayer ECM material, e.g., two or more layers of ECM materials coupled together, wherein each layer may comprise ECM materials in the same or different forms, and/or from the same or different sources. The layers may be bonded together or crosslinked, such as crosslinking multiple sheet layers together via a chemical process. Crosslinking can be achieved through various methods and processes generally known to one of ordinary skill in the art, including chemical and/or biochemical processes, temperature-based methods, pressure-based methods, processes that include exposure to light, and energy-based methods. Crosslinking may be achieved via differential crosslinking, e.g., by performing targeted crosslinking to achieve bonding of different tissue layers or ECM components at specific locations or regions. Crosslinking may be used to generate different elasticity properties and/or other mechanical properties at the crosslinked sites or regions, this allowing the composition to be tailored for a specific application, or to generate a desired size and/or shape for a specific application.

In some embodiments, the ECM materials may retain the structure of the native tissue. For example, a sheet may be produced by decellularizing native tissue that has a sheet-like structure, such as membrane layers (e.g., fascia or dermis) or submucosa, while a sponge or scaffold-like structure may be produced by decellularizing native tissue that has interstitial structure, e.g., organs such as the spleen, kidney, pancreas, or liver. Further, for example, rod-like ECM materials may be produced from native tissues having a generally rod-like or cylindrical structure such as tendons and nerves; and tubular ECM materials may be produced from native tissues have a tubular structure, such as blood vessels, the trachea, or the esophagus.

In some embodiments, the ECM materials or collagen-based materials may be manipulated or chemically altered into a form substantially different from the form of the native tissue. For example, the composition may comprise one or more ECM materials or collagen-based reduced to particulate form via grinding, crushing, milling, or other mechanical process. The particles may be used in the composition directly, or may be combined with a suitable liquid or gel to form a paste or dispersion for administration. Further, for example, one or more ECM materials may be dissolved into a liquid or gel, e.g., via enzymatic digestion or other biological or chemical process. The liquid or gel may be used in the composition directly, or may be combined with a suitable liquid or gel to form an emulsion for administration. In some embodiments, the structure of the ECM material(s) may be modified, e.g., via a chemical process to denature proteins of the ECM, to provide for increased porosity.

For particulate compositions (also referred to as powders herein), the particles may range from about 100 nm to about 2000 µm in diameter. The particle size distribution of a composition may be selected based on the desired application. For example, particles ranging from about 100 nm to about 5 µm in diameter, e.g., from about 1 µm to about 5 µm in diameter, may be suitable for administration via inhalation, while particles ranging from about 1000 µm to about 2000 µm in diameter may be suitable for use in filling voids or augmentation applications. Further, for example, particles ranging from about 50 µm to about 100 µm in diameter may be suitable for a variety of therapeutic injection applications, while particles ranging from about 100 µm to about 1000 µm in diameter may be suitable for topical wound applications, and particles ranging from about 10 µm to about 50 µm may be suitable for corneal repair applications (e.g., the particles being combined with a suitable liquid and delivered to the eye via a suspension, such as with eye drops). These size ranges are intended as general guidelines only, and may vary according to the medical application and/or particular needs of a patient.

In some embodiments, combinations of ECM materials may be manipulated into single composite form or construct. For example, pieces or strips of different ECM sheet materials coupled together to form a composite ECM material sheet. The pieces or strips of different ECM materials may be stitched, stapled, or coupled together with a suitable adhesive, or chemically cross-linked or bonded together. In some embodiments, the composition may comprise portions of sheet-like spleen ECM coupled to portions of sheet-like lung ECM, e.g., to form a composite ECM sheet. Similarly, portions of different ECM materials may be coupled together to form a single rod, tube, three-dimensional construct, mesh, sponge, or other suitable form of ECM material.

As mentioned above, the structures and components of different ECM materials may provide different benefits, such that combining two or more types of ECM materials may provide compositions uniquely tailored to the specific needs of a patient. The compositions may be designed to take advantage of the signaling components naturally occurring in the tissues from which the ECM materials are derived, including, but not limited to, VEGF, FGF, EGF, TGF-β, PDGF, and/or IGF.

For example, the composition may comprise two or more ECM materials in particulate form, with the ratios of the ECM materials adjusted to provide a composition with a desired content of desired components, including, but not limited to, growth factor and/or other signaling components. The composition may be applied in particulate form to a site in need of repair, or may be injected/applied as a suspension or particulates in combination with a carrier (e.g., liquid solution). Applications for particulate compositions include, but are not limited to, nerve repair, spinal disc repair, arthritis treatment, hair restoration, bone regeneration, bone augmentation, cartilage repair, tendon repair, ligament repair, burn treatment, myelin sheath regeneration, cornea repair, and lung repair.

Antimicrobial Agent(s)

In some embodiments, the composition may have antimicrobial properties, e.g., to reduce, eliminate, prevent, or otherwise control microbial activity upon application of the composition to a patient. For example, the composition may comprise one or more antimicrobial agents. Suitable antimicrobial agents include, but are not limited to, silver and compounds and alloys thereof (e.g., silver, silver oxide, silver nitrate, silver sulfazidine, silver-imidazolate, silver phosphate), zinc and compounds and alloys thereof (e.g., zinc, zinc chloride, zinc oxide, zinc sulfate monohydrate, zinc-hydroxyapatite, brass), copper and compounds and alloys thereof (e.g., copper, brass, bronze), bismuth and compounds and alloys thereof, biguanide compounds (e.g., polyhexamethylene biguanide, chlorhexadine, polyaminopropyl biguanide, alexidine), berizalkonium chloride, triclosan (5-chloro-2-(2,4-dichlorophenoxy)phenol), antibiotic drugs such as neomycin and bacitracin, honey, coconut, coconut-based products, essential oils, and plant extracts. In some embodiments, a combination of agents may be used, e.g., to provide a wide spectrum of antimicrobial activity. For example, the antimicrobial agent(s) may be effective against bacteria, yeast, fungi, and/or extracellular viruses. e.g., by inhibiting microbial cell activities, transport and/or reproduction. The antimicrobial agent(s) may be selected based on compatibility with other components of the composition and/or the medical needs of the patient. In some embodiments, the amount of antimicrobial agent(s) in the composition may be chosen based on the desired antimicrobial effect on the patient to be treated with the composition.

Antimicrobial agents may be applied to any surface of, or otherwise incorporated into, one or more ECM materials of the composition or the composition as a whole. While the following discussion will refer to deposition of antimicrobial agents on ECM materials generally, it is understood that the antimicrobial agents may be applied alternatively or additionally to multiple types of ECM materials simultaneously, such as application to a composition comprising different types of ECM materials.

The antimicrobial agent may comprise a solid, a liquid, a solution (e.g., a solid dissolved or dispersed in a liquid solvent), or a vapor. To deposit antimicrobial agents in liquid form, or a solid in solution, the ECM materials may be immersed in the liquid/solution or the liquid/solution applied to various portions of the ECM materials. The ECM materials may be dried, e.g., via evaporation, upon heating, under reduced pressure, in controlled humidity conditions or desiccation chambers, or under forced airflow. In the case of a solution, for example, evaporating the solvent may leave behind the solid antimicrobial agent as a deposit or thin layer on the ECM materials. In some embodiments, the antimicrobial-coated ECM materials may be broken down into smaller pieces or particles to be incorporated into a composition and/or for administration to a patient in particulate form. The antimicrobial agent may be chemically and/or biochemically bound to the ECM substrate.

The method of applying the antimicrobial agent(s) may be selected based on the form of the ECM materials or composition. In the case of a sheet, for example, an antimicrobial agent may be applied to either or both sides of the sheet. For a multilayer structure (see, e.g., FIGS. 1 and 3, discussed below), the antimicrobial agent may be applied solely to the outermost layers, a combination of outer and inner layers, or solely the inner layers. For example, a multilayer composition may be assembled by treating one or more sheets with an antimicrobial agent, layering the sheets to form multiple layers, and optionally crosslinking the layers together. In the case of a reticular or scaffold-like structure, the ECM matrix may be immersed in a solution comprising the antimicrobial agent, such that the solution may permeate the matrix, or the antimicrobial agent in particulate form may be directly incorporated into the matrix. In some embodiments, an antimicrobial agent may be localized within the ECM matrix by applying the solution to select portions of the matrix.

In some embodiments, the antimicrobial agent may be deposited from the vapor phase. For example, the antimicrobial material to be deposited may comprise crystals having a crystalline lattice structure generated in the vapor phase, e.g., via evaporation or sputtering, and transported into a volume in which the temperature is controlled. Atoms of the antimicrobial material may collide with the working gas, causing them to lose energy, such that the antimicrobial material is condensed from the vapor phase onto a cooled substrate, such as a liquid nitrogen-cooled finger. For silver, deposition may be conducted at low substrate temperatures, e.g., ranging from about −10° C. to about 100° C.

In some embodiments, the composition may comprise silver particles (microparticles and/or nanoparticles). The silver may be in ionic form, e.g., particles comprising a silver salt. The silver may be applied as a spray coating or added as a solution to the ECM materials and then dried. For example, the silver particles may be dispersed in water or other solvent to form a solution, the solution applied to one or more surfaces of the ECM materials, and the solvent allowed to evaporate such that the silver particles remain as an antimicrobial coating on the ECM materials. Further, for example, the particles may be embedded directly within an ECM matrix without dispersing the particles in solution. In some embodiments, the composition may comprise silver-coated ECM particles, e.g., produced by coating ECM particles or reducing coated-ECM materials to particulate form. In some embodiments, silver can be applied by other coating methods such as ion beam deposition. The silver can be incorporated before or after the ECM materials are dried (e.g., following a decellularization process), or may be incorporated into a particulate, liquid, emulsion, or gel form of the ECM materials.

In some embodiments, the silver content of the ECM materials (surface concentration) may range from about 1 mg/100 cm$^2$ to about 1000 mg/100 cm$^2$, such as from about 1 mg/100 cm$^2$ to about 100 mg/100 cm$^2$. In some embodiments, the silver content of the ECM materials (mass concentration) may range from about 1 mg/g to 100 mg/g, such as from about 1 mg/g to about 20 mg/g. In some embodiments, the silver may provide a coating on the ECM materials, wherein the thickness of the silver coating may range from about 100 Å to about 5 μm, such as from about 500 Å to about 2 μm.

Exemplary Administration/Applications

Compositions according to the present disclosure may be designed for external and/or internal administration to a patient. The compositions may be applied to an anatomical site other than that of the ECM source material(s), or to the same anatomical site(s). The patient tissue in need of repair, augmentation, or regeneration may include, but is not limited to, skin, muscle, tendon, ligament, nerve, vascular, dura mater, cornea, bone, heart, liver, lung, spleen, pancreas, stomach, intestine, or brain tissue. The ECM materials may be derived from tissue that is allogeneic, autologous, or xenogeneic to the patient being treated.

In some embodiments, at least a portion or the entire composition may be biodegradable/resorbable, e.g., such that the composition need not be removed after application or implantation into a patient. For example, at least a portion of the composition may be configured to be absorbed or resorbed, to dissolve, or to degrade within about 24 hours, 48 hours, 72 hours, 1 week, 2 weeks, 1 month, 3 months, or 6 months of application or implantation. The ECM materials may be entirely resorbable, only partially resorbable, or non-resorbable. For example, the ECM materials may be processed to modify their absorption characteristics, such as via crosslinking with glutaraldehyde or other suitable crosslinking agent. In addition to ECM materials, which may be resorbable or non-resorbable, the composition may comprise one or more natural or synthetic resorbable/biodegradable materials, such as collagen, hydroxylapatite, polylactides, polyglycolides, polycaprolactones, hyaluronic acid, gelatin, bioactive glass, tricalcium phosphate, soft tissue allografts, or hard tissue allografts.

The composition may be configured for temporary application, e.g., a temporary bandage or implantable medical device, to be removed after a certain amount of time, such as after about 1 week, 2 weeks, 1 month, 3 months, 6 months, 9 months, or 1 year. For example, the composition may comprise a hemostasis bandage to help stop bleeding of a wound, such that the bandage may be removed once bleeding has stopped and/or for surgical repair of the wound. Further, for example, the composition may comprise a coating on a medical device configured for temporary implantation in the body, such as a stent or a catheter, or a pacemaker lead intended to be removed at a later date. The ECM materials of the coating may help to prevent infection (e.g., in conjunction with an antimicrobial agent of the composition), and/or may facilitate contact between the medical device and the native tissue of the patient.

In some embodiments, the composition may be configured for permanent implantation, not to be removed from the patient, and/or may comprise a coating of a medical device configured for permanent implantation. Similar to the above, coatings used for permanent implantation of a medical device may help to prevent infection and/or facilitate contact with native tissue of the patient.

Embodiments of the present disclosure include identifying a site of defect or wound, e.g., in mammalian tissue, such as in a patient, providing a composition comprising two or more ECM materials (e.g., spleen ECM in combination with one or more of lung ECM, gall bladder ECM, bone marrow ECM, pancreas ECM, or liver ECM), contacting the site with a therapeutically-effective amount of the composition, and healing or regenerating tissue at the site. In some embodiments, the composition may comprise an antimicrobial agent such as ionic silver.

Compositions according to the present disclosure may include one or more therapeutic agents and/or one or more pharmaceutical agents. The types and amounts of therapeutic agents and/or pharmaceutical agents may be chosen based on the desired therapeutic or pharmacological effect(s) on a patient to be treated with the composition. Exemplary therapeutic agents may include, but are not limited to, moisturizing agents, drying agents, and soothing agents. Exemplary pharmaceutical agents include, but are not limited to, steroids, hormones, analgesics, anti-inflammatory agents, and chemotherapy drugs. Pharmaceutical and therapeutic agents may be chosen based on the intended application of the composition. For example, the composition may comprise a pharmaceutical agent to help prevent narrowing (stenosis) of blood vessels for vascular applications, or to help prevent cell adhesion, e.g., by serving as an adhesion barrier for hernia repair or other internal body cavity repair applications. The compositions may be used for drug delivery, to deliver one or more pharmaceutical agents to a specific anatomical site or area. For example, the compositions may be tailored to dissolve, degrade, or be absorbed by the body at a rate that allows for elution of one or more pharmaceutical agents at a controlled or desired rate, e.g., to deliver a pharmaceutically-effective amount of the pharmaceutical agent(s). In some embodiments, the composition may comprise small "pellets" or dense cylinders of ECM dosed with one or more chemotherapy drug(s). The composition may be formulated for injection or to be surgically implanted at a tumor site, such that the composition releases the drug(s) at the desired site, while limiting or minimizing trauma due to exposure to other tissues and/or body-system-wide side effects.

The following describes various exemplary compositions, including different forms and combinations of ECM materials, and methods of use thereof. While some of the examples describe combinations of specific types of ECM materials (e.g., spleen and lung ECM), other combinations of ECM materials are likewise possible and encompassed herein.

The composition may comprise one or more ECM materials in sheet form, including sheets with particular texture or structure to promote tissue growth, such as a mesh-like or scaffold-like structure. For example, the composition may include a scaffold-like structure for promoting restoration of tissue when implanted at anatomical site in a patient. The composition may have a multilayer configuration (e.g., two or more sheet layers bonded, crosslinked, or otherwise coupled together), and/or a sandwich configuration (e.g., two or more sheets bordering or enclosing a material therebetween, or a single sheet folded over on itself to encase a material). The composition may be designed for external application, internal application, or both. In some embodiments, the sheets may be treated with an antimicrobial agent as discussed above to provide the composition with antimicrobial properties.

Figure 2:
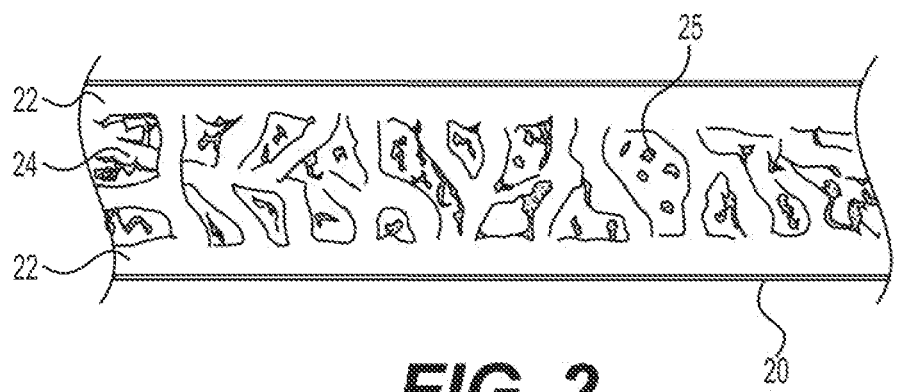
FIG. 2 shows an exemplary composition, in accordance with one or more embodiments of the present disclosure.

FIGS. 1 and 2 illustrate exemplary compositions comprising ECM sheet materials in accordance with the present disclosure. FIG. 1 shows a multilayer composition 10 comprising layers that have different types of tissue structure. As shown, the composition may comprise a first layer 12 of ECM material having a sheet-like structure, and a second layer 14 of ECM material having both sheet-like and reticular, fibrous matrix-like structure. In some embodiments, the second layer 14 may comprise only matrix-like structure. The two layers may be derived from the same type of tissue (e.g., a sheet-like layer and matrix layer of spleen ECM coupled together) or different types of tissues (e.g., a sheet-like layer of lung ECM coupled to a reticular layer of spleen ECM). The composition may comprise more than two layers, e.g., alternating sheet-matrix layers, two or more sheet-like layers, two or more matrix layers, etc.

In some embodiments, for example, the composition may comprise a tissue graft or wound dressing (e.g., a bandage, patch, pad, compress, medical tape, etc.) that includes an outer sheet layer of lung ECM and inner matrix layer of spleen ECM, thus combining outer liquid impermeability from the lung ECM with an inner intricate network from the spleen ECM capable of accommodating materials to promote cell regeneration.

FIG. 2 shows an exemplary composition 20 comprising ECM materials having both sheet-like structure and matrix structure. For example, the ECM materials may be derived from spleen tissue, such that during the decellularization process the fibrous network or matrix structure 24 remains intact and attached to the membrane layer 22 on either side of the reticular matrix 24. The composition 20 may comprise a second type of ECM material 25 incorporated into the interstitial spaces within the reticular matrix structure 24. For example, the composition 20 may comprise particles of lung ECM and/or bone marrow ECM embedded within the reticular spleen matrix, a combination of lung ECM and spleen ECM particles, a combination of lung ECM in particulate form and in gel form, or a combination of lung ECM in particulate form and spleen ECM in gel form.

Compositions comprising sheet-like ECM materials (optionally in combination with other forms of ECM materials) may be used in a variety of applications. For example, a composition suitable for treating burns or skin lesions may comprise two or more layers of different ECM sheet-like materials (e.g., spleen ECM and lung ECM in sheet form), for example, wherein the sheets may be meshed or unmeshed. Silver (e.g., elemental or ionic silver) may be added as a coating or incorporated into the sheets to provide antimicrobial properties.

Further, for example, the composition may comprise a vascular patch or graft comprising one or more inner layers of lung ECM in sheet form, and one or more outer layers of spleen ECM in sheet form. For example, lung ECM may comprise the innermost 1-3 layers to provide a less permeable barrier and allow for faster endothelial cell migration across the inner portion of the patch/graft, while also utilizing the elastin in the lung ECM for better compliance matching of the patch/graft to the native blood vessel wall. Spleen ECM may comprise the outermost 1-3 layers to provide additional growth factors and a more porous outer layer to allow for faster host tissue incorporation.

In some embodiments, the composition may comprise a dura mater repair patch, comprising one or more inner layers of lung ECM in sheet form, and an outer layer of spleen ECM in particulate or gel form coated onto the sheet. The lung ECM sheet(s) may provide a relatively smooth and less porous surface adjacent to the cerebral spinal fluid, while the spleen ECM particulate or gel may provide more growth factor content for signaling.

In some embodiments, the composition may comprise a cornea repair patch, comprising one or more layers of lung ECM (e.g., in thin sheet form) combined with spleen ECM particulates. The lung ECM component may act as a patch while the particulate spleen ECM component may degrade more rapidly to provide a bolus of growth factor or other signaling components released at the injury/repair site.

The composition may comprise a guided bone regeneration (GBR) graft or guided tissue regeneration (GTR) graft. For example, the composition may comprise lung and spleen ECM in sheet form, the lung ECM placed adjacent to the bone to provide a less permeable barrier maintaining space for the bone to grow, and the spleen ECM comprising outer layers to provide a more porous ECM scaffold that allows for faster tissue ingrowth.

In some embodiments, the composition may comprise a hernia repair graft comprising multiple layers of both lung and spleen ECM materials in sheet form to provide sufficient strength for the specific hernia repair. Inguinal, hiatal, and ventral hernias each have different strength requirements due to the stresses at those particular anatomical sites. More strength is typically required for a ventral hernia repair device than a hiatal hernia repair device, for example. One side of the composition may comprise multiple layers of lung ECM sheet material to provide a less porous surface to minimize adhesion formation, while the opposite side may comprise multiple layers of spleen ECM sheet material to provide a more porous interface for rapid tissue ingrowth into the graft. The composition may comprise silver (e.g., elemental or ionic silver) and/or one or more other antimicrobial agents to provide antimicrobial properties.

In some embodiments, the composition may have a tubular or rod-like shape. For example, sheet-like ECM materials may be rolled or otherwise manipulated into a tubular configuration or rod-like shape. Tubular and/or rod-like ECM compositions may be tailored for a variety of anatomical applications.

For example, the composition may comprise a tubular nerve guide/graft including one or more inner layers of lung ECM sheet material and one or more outer layers of spleen ECM sheet material. The smoother surface of the inner lung ECM portion may provide a conduit suitable for the nerve to grow together, for example, while the outer spleen ECM portion may allow for incorporation of the graft into surrounding tissue. In some embodiments, the tubular ECM composition may further comprise one or more ECM materials inside the tubular surface (e.g., an ECM particulate material, ECM gel, or combination ECM particulate/gel), e.g., wherein the inside ECM material may degrade over time to release growth factors to stimulate tissue growth, such as new nerve growth. Exemplary applications for tubular ECM compositions include, but are not limited to, vascular grafts, vascular access devices, nerve guides, bile duct repair, ureter repair, urethra repair, and fallopian tube repair.

As mentioned above, the composition may comprise ECM sheet material rolled up into cylindrical shape, or twisted or braided into a strand or rod-like shape. In some embodiments, compressed ECM particulate, particulate/gel, or other suspension, dispersion, or fluidized ECM material may be placed into a mold and compressed into a rod-like shape or other three dimensional shape. The rod-like ECM material may include one or more other components, such as additional bioactive components, pharmaceutical agents, other ECM materials, polymers, hydrogels, hyaluronic acid, or allograft materials. Exemplary applications for rod-like ECM compositions include, but are not limited to, tissue grafts, tissue augmentation, and tissue reconstruction.

Figure 3A:
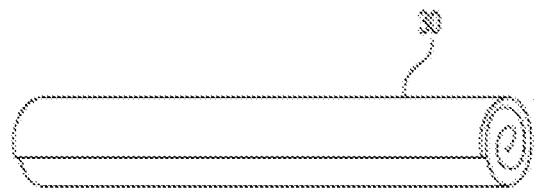
Figure 3B:
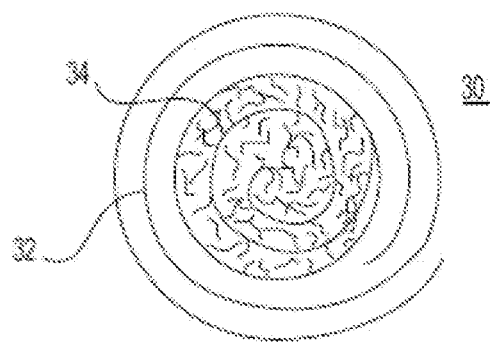
Figure 3C:
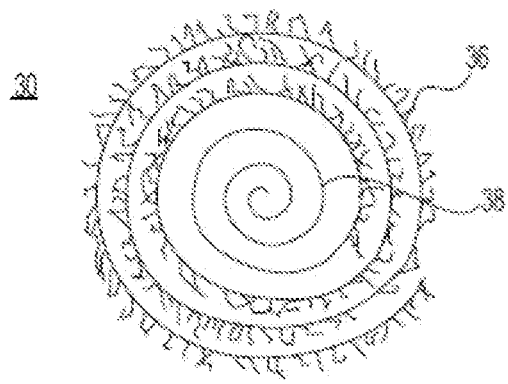

In some embodiments, the composition may comprise ECM materials in a rod-like shape, e.g., for use as a nerve graft or other tissue graft. An exemplary rod-like or cylindrical composition 30 is illustrated in FIGS. 3A-3C. For example, the composition 30 may comprise one or more layers of ECM material rolled into a generally cylindrical shape, as shown in FIG. 3A. FIGS. 3B and 3C show cross-sections of different possible configurations of the composition 30.

In some embodiments, for example, spleen ECM in sheet form may be rolled into a cylinder, with lung ECM in sheet form forming one or more outer layers surrounding the spleen ECM. This configuration is illustrated in FIG. 31B, showing one or more outer layers 32 of sheet-like lung ECM, and one or more inner layers 34 of reticular spleen ECM. In some embodiments, the composition 30 may comprise spleen ECM inside with lung ECM outside twisted or braided into a rod-like shape as well. The more porous portion of the spleen ECM on the interior of the composition 30 may provide for rapid tissue ingrowth through the center of the graft. The less porous lung ECM on the outside may provide for rapid cell migration across the surface of the graft while also preventing adhesion to native tissue and/or tissue ingrowth into the nerve gap being regenerated within the interior. FIG. 3C shows a cross-section of another exemplary configuration of the composition 30, comprising one or more outer layers 36 of sheet-like ECM material (e.g., sheet-like lung ECM), and one or more inner layers 38 of reticular ECM material (e.g., reticular spleen ECM). In some embodiments, allograft nerve tissue may be incorporated into the composition 30, e.g., as part of a twisted or braided outer strand, or as the center of a rolled cylinder rod shape nerve graft.

Rod-like compositions also may be used in tissue augmentation, e.g., during plastic surgery or reconstructive surgery. For example, the composition may be used in lip augmentation. Lung ECM may be used as the interior layers of a rod-shaped composition to form a less compressible core of the rod, allowing it to keep its shape and bulk, while spleen ECM may be used on the outside, so that the more porous spleen ECM surface faces outwards. The porous spleen ECM may allow for rapid tissue integration into the graft, resulting in less migration of the graft and faster healing.

Further, for example, the composition may have a cylindrical or rod-like shape used for nipple reconstruction. Depending on the surgical procedure used, the composition may be constructed with lung ECM on the interior to provide a less porous core, and spleen ECM on the outside to provide a more porous surface that can integrate with host tissue to keep the graft in place and maintain a protruding shape. In some embodiments, the composition may comprise spleen ECM on the inside, e.g., for tissue integration into the center of the composition to provide stability, and lung ECM on the outside, e.g., to provide for less host tissue invasion and better preserve the shape and volume of the protrusion. In some embodiments, the composition may comprise a twisted or braided strand of both lung ECM and spleen ECM.

In some embodiments, rod-like ECM material may be used as a tendon or ligament graft. For example, the composition may comprise spleen ECM and lung ECM in different amount, such as a spleen:lung ratio of about 70:30, 80:20, or 90:10, wherein spleen ECM comprises the inside layers, and lung ECM comprises the outer layers. As mentioned above, lung ECM generally has a higher elastin content and stretches more than spleen ECM. A tendon or ligament graft typically requires minimal stretching to prevent the joint from becoming "loose" over time due to the tendon or ligament stretching after implantation of the graft. However, during healing, ECM grafts often shrink slightly. An amount of stretching therefore may be desired, e.g., by incorporating lung ECM within the outer layers of the graft. The amount of lung ECM incorporated into the graft may be adjusted to achieve the degree of stretching desired. In some embodiments, the graft composition may comprise allograft tendon or ligament. Incorporating ECM materials, e.g., in sheet, particulate, and/or gel forms, into the tendon or ligament graft composition may provide additional scaffolding and signaling components for incorporation of the tendon/ligament into the host tissue and for cell migration and proliferation in the composite graft material.

The composition may comprise a compressible or expandable, rod-like shape, e.g., for implantation as a medical device, e.g., for vascular access site repair. Typically, compression is applied to vascular access sites to prevent bleeding and close the site. A rod-like or cylindrical composition comprising spleen and lung ECM (and/or other types of ECM materials) may be inserted into the access site, e.g., to fill and/or seal an incision in a blood vessel and stop any bleeding, while also providing a scaffold and biological signaling components to heal the incision into the blood vessel. For example, the composition may comprise a rolled cylinder with one or more inner layers of lung ECM (e.g., rolled sheets of lung ECM) to provide a less compressible or non-compressible core, and one or more outer layers comprising more porous spleen ECM in sheet form. The composition may be compressed into a cylindrical shape configured to expand when wetted with blood at the site, thus sealing the incision. Further, for example, lung and spleen ECM in gel form may be dried and/or crosslinked into a cylindrical shape, wetted, compressed, and dried again to produce an expandable sponge having a generally cylindrical or rod-like shape.

In some embodiments, the composition may comprise a medical device that includes one or more features configured to anchor the device upon implantation in the body, e.g., as a fistula plug. For example, high output fistula defects can cause fistula plugs or other materials/devices to dislodge from the defect. To address this problem, the device may comprise a combination of spleen and lung ECM materials in a cylindrical or rod-shaped body portion with protrusions along the length of the cylindrical/rod-shaped body to anchor the device against the walls of the fistula and prevent the device from becoming dislodged. This anchoring may also provide for close tissue approximation to allow for tissue ingrowth into the ECM materials (e.g., ECM matrix) via the scaffolding structure and the biological signaling components.

Figure 4A:
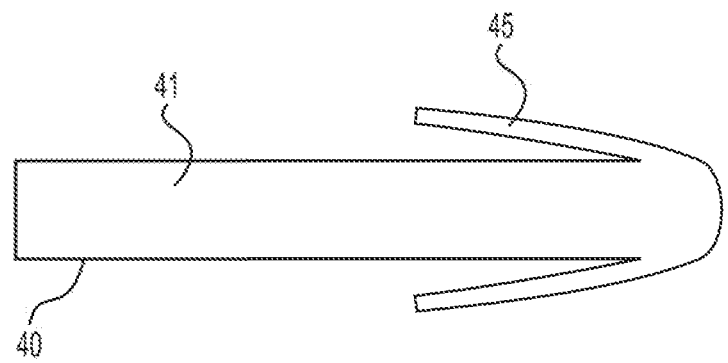
FIGS. 4A and 4B show an exemplary composition according to one or more embodiments of the present disclosure.
Figure 4B:
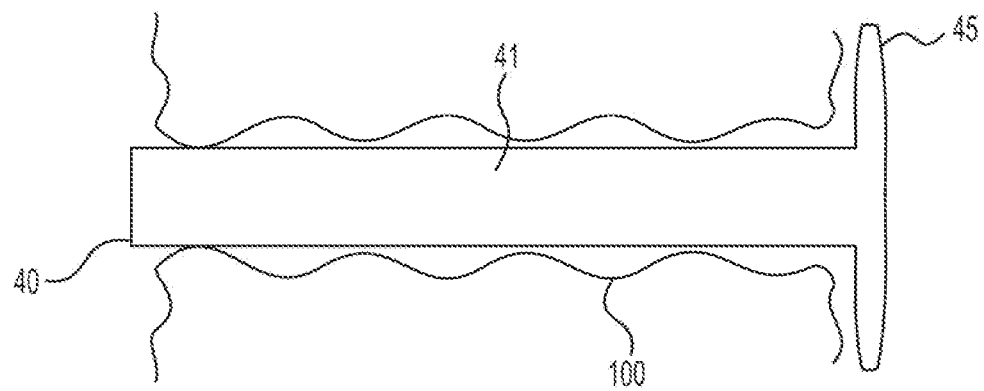

In some embodiments, for example, the device may have an "umbrella" shape formed by expandable arms at one or both ends of the device. When inserted into the fistula and deployed, the "umbrella" end may open into a disc or similar shape coupled to the cylindrical/rod-shaped body portion in order to seal one end of the fistula and anchor the device, e.g., to repair a defect. This configuration is illustrated in FIGS. 4A and 4B, showing a medical device 40 configured for anchoring upon implantation in a fistula or other passage within the body. The device 40 may include a body portion 41 and at least one anchoring portion 43. For example, the body portion 41 may comprise a composition in accordance with FIG. 3A, e.g., comprising inner and outer layers of different ECM materials, or any other combination of ECM materials as described herein. The anchoring portion 43 may comprise a set of expandable arms 45 on opposite sides of the body portion 41. In some embodiments, the device 40 may comprise more than one anchoring portion 43.

Each of the body portion 41 and the anchoring portion 43 may comprise one or more ECM materials and/or one or more non-ECM materials. Non-ECM materials may include, but are not limited to, biocompatible metals, metal alloys, ceramics, polymers, or combinations thereof. Suitable polymers include, but are not limited to, polylactic acid (PLA), polyglycolide (PGA), and poly(lactic-co-glycolic acid) (PLGA). The body portion 41 may comprise the same or different materials as the anchoring portion 43. For example, the body portion 41 may comprise a combination of two or more different ECM materials, and the anchoring portion 43 may comprise at least one non-ECM material, such as a polymer or combination of polymers. In some embodiments, the body portion 41 and the anchoring portion 43 both may comprise at least two different ECM materials. Any of the ECM materials, combinations of ECM materials, and non-ECM materials (including antimicrobial agents) as discussed above may be used for the medical device 40.

When the device 40 is in a compressed configuration, as shown in FIG. 4A, the arms 45 may extend substantially alongside the body portion 41 to facilitate insertion into a fistula 100 or other passageway within the patient's body. The arms 45 may be configured to expand away from the body portion 41 via self-expansion once no longer restrained by the walls of the fistula 100. Once expanded, as shown in FIG. 4B, the arms 45 may anchor the device 40 within the fistula 100.

Figure 5A:
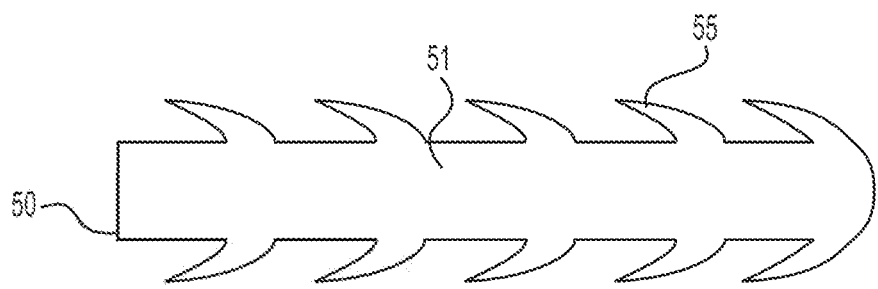
FIGS. 5A and 5B show an exemplary composition according to one or more embodiments of the present disclosure.
Figure 5B:
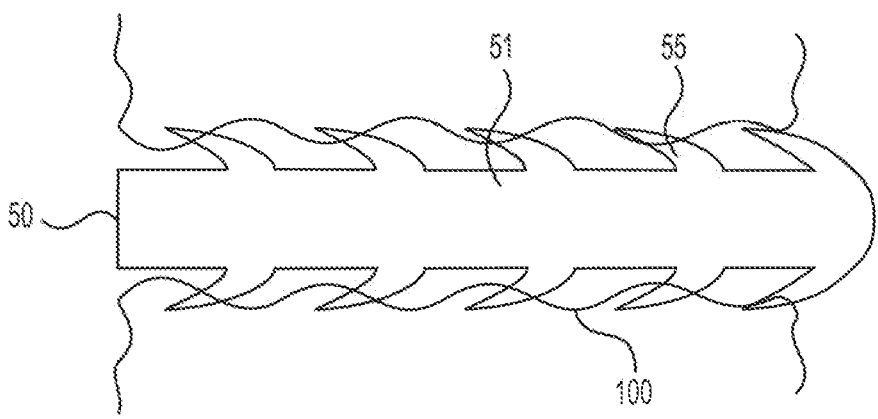

Further, for example, the composition may comprise a medical device with a cylindrical or rod-like body portion that includes flanges, "wings," or protruding edges along at least a portion of the length of the body. FIGS. 5A and 5B illustrate an exemplary medical device 50 including a body portion 51 and one or more protrusions 55 along the length of the body portion 51. The body portion 51 may comprise two or more different types of ECM materials, such as the composition 30 of FIG. 3A, or any other combination of ECM materials and non-ECM materials as described herein, including the materials discussed above in connection to medical device 40. The protrusions 55 may be angled in a proximal direction (i.e., away from the direction of insertion), such that the device 50 may be advanced within the fistula 100 but not withdrawn, due to the protrusions 55 catching tissue along the wall of the fistula 100. In some embodiments, the protrusions 55 may have a pointed or barbed tip to further anchor the device 50 within the fistula 100.

Inhalation

In some embodiments, the composition may comprise ECM materials in particulate form, e.g., for administration via inhalation. The particles may range from about 100 nm to about 5 µm in diameter, such as from about 1 µm to about 5 µm in diameter, or from about 100 nm to about 2.5 µm in diameter. In some embodiments, for example, the composition may comprise particles having substantially the same size, e.g., a particle diameter of about 100 nm, about 300 nm, about 500 nm, about 1 µm, about 2.5 µm, or about 5 µm. In some embodiments, the composition may comprise particles having a size distribution with an average or median diameter ranging from about 300 nm to about 5 µm, e.g., about 300 nm, about 500 nm, about 1 µm, about 2.5 µm, or about 5 µm. The size distribution may be unimodal or bimodal.

The composition may comprise two or more ECM materials in particulate form. For example, the composition may comprise a first set of particles of a first ECM material, and a second set of particles of a second ECM material, wherein the first and second sets of particles may have the same or different diameters or size distributions. In some embodiments, the composition may comprise particles of lung and spleen ECM ranging from about 1 µm to about 5 µm in diameter for delivery to the lungs of a patient via inhalation.

The particulate composition may be used to treat the respiratory system, to treat a respiratory disorder, and/or to deliver a pharmaceutical agent such as a steroid for uptake via the respiratory system. In some embodiments, for example, the composition may be used to treat asthma, lung infections, or a lung injury, such as damage to the lungs from inhalation of damaging gases, smoke, or chemical or biological agents. The composition may be inhaled after exposure to toxins and harmful substances to help heal damaged tissue in the lungs, and to minimize and/or prevent lung fibrosis. In some embodiments, the composition may be administered to mitigate the effects of diseases that cause damage to the lungs, e.g., as part of a routine dosing regimen.

In some embodiments, the composition may serve as a delivery vehicle for a pharmaceutical or therapeutic agent. For example, the pharmaceutical or therapeutic agent may be incorporated into the ECM material during processing such that the agent is associated with the particles, such as a coating. In at least one embodiment, the composition may comprise at least one ECM material in combination with fluticasone propionate and salmeterol, optionally in combination with a pharmaceutical agent such as a steroid, formulated for administration via inhalation.

Injection

The composition may be formulated for injection, e.g., in liquid or gel form. ECM particulates, gels, and/or particulate and gel combinations may be used as an injectable for a variety of applications, including, but not limited to arthritis (e.g., joint injections to treat arthritis), tendon/ligament partial tears, cartilage tears or damage, nerve tears or damage, myelin sheath regeneration, hair restoration, and in plastic and reconstructive surgery (e.g., as a void filler or bulking agent). As mentioned above, ECM gels may be produced by digesting (e.g., via digestive enzymes) or chemically processing ECM materials into gel form, which may be combined with ECM particles or other additional ECM materials.

In some embodiments, the composition may comprise a 50-50 ratio of particulate lung ECM and particulate spleen ECM suspended within an ECM gel as a carrier (e.g., a lung ECM gel, spleen ECM gel, or lung/spleen mixture ECM gel). The lung/spleen composition may be injected at one or more sites along a nerve that has been damaged or sustained loss of the myelin sheath, such as in amyotrophic lateral sclerosis (ALS) disease or multiple sclerosis. Without being bound by theory, it is believed that growth factors and other signaling components within the ECM composition may signal mesenchymal stem cells to migrate to the site of injection and induce formation of new myelin sheath or nerve tissue.

Three-Dimensional Constructs

In some embodiments, the composition may comprise ECM materials formed into a three-dimensional construct, e.g., to fill or repair large defects, or in patient-specific reconstruction of lost or damaged tissue. Such constructs may be useful in reconstructive surgery, wherein there may be a need to fill a void, or to regenerate tissue in a specific area, e.g., having a particular shape.

In some embodiments, for example, the ECM constructs may have three-dimensional shapes obtained via specialized forms or molds, or by cutting, trimming, or otherwise manipulating larger, standardized shapes such as blocks or rods into the desired form, e.g., to match the size and shape of the void or defect to be filled. The construct may vary in composition, e.g., comprising a composite of two or more ECM materials, and may vary in porosity. The construct may comprise one or more non-ECM components, including, but not limited to, cells, pharmaceutical agents, polymers, or demineralized bone.

In some embodiments, scanning, imaging techniques, and/or 3D computer modeling may be used to prepare a replica of the void/defect or otherwise obtain the dimensions of the ECM construct needed for repair. In this way, a three dimensional construct may be made according to the exact dimensions needed for a given patient. The mold may be filled with different types of ECM materials and non-ECM materials to obtain a patient-specific implant.

For example, a patient with oral cancer may require surgical intervention to remove bone and soft tissue at the site of the cancer. To repair the affected area after surgery, e.g., by implanting replacement tissue or a tissue graft, a mold may be designed by imaging the removal site. A combination of lung ECM and spleen ECM in particulate and gel form may be added to the mold, e.g., to comprise the soft tissue portion, along with demineralized bone, e.g., to comprise the replacement jaw bone.

Additional combinations of ECM materials may include ECM sheets combined with one or more other ECM materials in particulate, gel, foam, and/or sponge form to create "sheet-like" constructs with varying densities and compressibility. The constructs may be tailored for specific applications, including, but not limited to, cartilage repair grafts and spinal disc grafts. In some embodiments, for example, the composition may comprise circular sheets of lung and/or spleen ECM materials with other forms of ECM materials (e.g., in particulate, gel, particulate plus gel, foam, or sponge form, or similar materials) that provide an inner circular portion that is more compressible than the outer "ring" of the lung/spleen ECM material. This configuration may simulate the annulus on the outside (e.g., the anlus fibrosus) and the nucleus on the inside (e.g., the nucleus pulposus). In some embodiments, the composition may be a hemostasis device comprising an outer layer of lung ECM (e.g., to provide liquid impermeability), an inner layer of spleen ECM (e.g., processed to maintain the unique architecture of the reticular spleen ECM structure), and a coating of lung/spleen ECM particulate mix incorporated into the inner spleen ECM layer. The ratio of the particulate may be about 50:50 lung-spleen.

Further, the composition may be used as a bone graft material. For example, the composition may comprise a particulate mix of two or more ECM materials (e.g., spleen and lung ECM) in various ratios, or a mix of an ECM material in particulate form and an ECM material in gel form (e.g., spleen ECM particulate and lung ECM gel, or lung ECM particulate and spleen ECM gel). The composition may include more or more additional agents or materials such as, e.g., tricalcium phosphate, hydroxyapatite, bioactive glass, mineralized bone, demineralized bone, or another mineral component. In some embodiments, the composition may include one or more antimicrobial agents such as, e.g., ionic silver or elemental silver, for use in bone infection healing applications.

The ECM materials may be combined or incorporated into each other and/or combined with non-ECM materials via any suitable method, and may be physically attached and/or chemically bonded together. For example, an adhesive such as fibrin glue, cyanoacrylate, thrombin/gelatin, polyethylene glycol (PEG), or a solder such as albumin (e.g., applied with laser energy or heat to weld tissues together) may be used to incorporate ECM materials into each other. Further, cross-linking agents such as, e.g., glutaraldehyde, dendrimers, or methylene blue, may be used to form bonds between different ECM materials. Additionally or alternatively, ECM materials may be combined in a composition via thermal energy, ultra-violet light, and/or chemical cross-linking. For example, sugar-based molecules such as a saccharide (e.g. glucose or galactose) or a disaccharide (e.g. lactose or sucrose) and/or peptide-based molecules may be used to combine different ECM materials. In some embodiments, different ECM materials may be combined into a three-dimensional construct form by exposing the materials to heat (e.g., a temperature ranging from about 50° C. to 250° C.) while they are compressed or in close proximity to each other. The heat may generate bonds (crosslinks) between collagens in the different ECM materials.

In some embodiments, the composition may be prepared by combining an ECM materials in gel form with an ECM material in particulate form, e.g., to produce a particulate wafer or cake. For example, the ECM gel may be introduced into a mold with the ECM particulate, compressed and/or cross-linked together, and dried in a mold to form the composition in a particulate wafer or cake. In some embodiments, the ECM gel may be introduced into a mold without ECM particulate, and compressed and/or cross-linked to form the composition.

Compositions according to the present disclosure may be prepared by mixing different ECM materials together in particulate form. ECM particulates may be prepared by chopping, cutting, pulverizing, milling, or grinding the ECM material with a suitable device such as a blender, a hammer mill, a knife mill, a centrifugal mill, or a roller crusher, for example, to form particles. In some embodiments, two or more ECM materials in particulate form may be mixed together in a gel (e.g., an ECM material in gel form, which may be the same or different type of ECM material as the ECM particulates) or a liquid carrier. Examples of suitable carriers include, but are not limited to, hyaluronic acid, gelatin, lecithin, collagen gel, and saline.

Further, compositions according to the present disclosure may be prepared by coating one type of ECM material onto a different type of ECM material. For example, a first ECM material (e.g., an ECM core) may be coated with a second ECM material (e.g., an ECM coating). For example, the composition may comprise ECM particles having a core of one type of ECM material and a coating of a different type of ECM material. Coating the ECM core may be performed, for example, by precipitating the second ECM material onto the first ECM material from a solution, by a roll coater, or by a granulator. The second ECM material used as the coating may be in a liquid or gel form. Other materials suitable coating ECM materials may include, but are not limited to, PLGA, hyaluronic acid, collagen, or a mixture thereof.

In some embodiments, the composition may comprise ECM materials in gel form, wherein the gel may change in response to a stimulus. For example, the gel may expand in vivo when injected into a target site and/or may polymerize in vivo, and thus may stay fixed into position when polymerized. The stimulus may be, e.g., a change in temperature and/or pH. In some embodiments, for example, the gel may comprise two or more different ECM materials and at least one temperature-responsive polymer, copolymer, or block copolymer. For example, the gel may polymerize after a change in pH, wherein the pH may be altered by adding an acid or base such that the gel polymerizes in vivo at the application site. In some embodiments, the gel may be designed to polymerize at body pH after application to the desired site. Different ECM materials may be delivered to the target site concurrently in gel form, in solution, or as particulates suspended in a carrier, such that once the ECM materials are mixed together at the target site, they polymerize and/or expand.

Other embodiments of the present disclosure will be apparent to those skilled in the art from consideration of the specification and practice of the embodiments disclosed herein. While various examples provided herein illustrate specific types of ECM materials and combinations thereof, one of ordinary skill in the art will recognize that other types of ECM materials from any tissue source and combinations of ECM materials also may be used. Further, any features of an embodiment disclosed herein may incorporated into any other embodiment.

The following examples are intended to illustrate the present disclosure without, however, being limiting in nature. It is understood that the present disclosure encompasses additional embodiments consistent with the foregoing description and following examples.

EXAMPLES

Example 1

Samples of porcine tissues were extracted to measure growth factor content. Dried micronized matrix material sampled from pig stomach, spleen, and lung tissues were extracted for 72 hours at 4° C. Three different buffers were used in the extractions: phosphate buffered saline (PBS), RIPA buffer, and 0.5 M acetic acid (AA). Each extraction included a 20:1 extraction volume to tissue weight ratio (6.0 ml extraction buffer for 300 mg matrix material). Extracts were analyzed for VEGF-A, EGF, bFGF, PDGF, IGF1, and TGFβ by ELISA using the individual ELISA instruction manual. In order to assay acetic acid extracted samples using ELISA, acetic acid extracts were neutralized by adding 219 μl of 2.5 M Tris base per 1.0 ml of acetic acid extract. Results are shown in Table 2.

TABLE 2

Growth factor concentrations (ng/ml) measured in porcine stomach, spleen, and lung tissues.

| | Stomach | | | Spleen | | | Lung | | |
|---|---|---|---|---|---|---|---|---|---|
| Extraction | PBS | RIPA | AA | PBS | RIPA | AA | PBS | RIPA | AA |
| VEGF | 435.8 ± 18.6 | 314.7 ± 8.7 | 523.7 ± 78.9 | 411.1 ± 7.3 | 328 ± 19.4 | 437.2 ± 62.4 | 190.1 ± 10.9 | 157.8 ± 6.1 | 569.6 ± 136.8 |
| EGF | 177.1 ± 117.8 | 96.3 ± 36.6 | 112.2 ± 38.2 | 260.4 ± 31.6 | 249.2 ± 31.7 | 206.8 ± 24.5 | 252.7 ± 78.2 | 178.1 ± 38.2 | 174.6 ± 51.2 |
| bFGF | * | * | 28.7 | * | * | 50.1 | * | * | 54.0 |
| PDGF | 303.1 | * | 168.8 | 324.5 | * | 318.6 | 303.2 | * | 245.3 |
| IGF1 | * | 3.1 | 20.8 | 3.1 | 11 | 79.6 | 1.7 | 6.4 | 141.7 |

* not detected

It is intended that the specification and examples be considered as exemplary only, with a true scope and spirit of the present disclosure being indicated by the following claims.

What is claimed is:

1. A composition comprising:
spleen extracellular matrix in particulate form, wherein the spleen extracellular matrix comprises native growth factors retained from spleen tissue, wherein the native growth factors retained from spleen tissue include epidermal growth factor and vascular endothelial growth factor; and
lung extracellular matrix in particulate form, the lung extracellular matrix being derived from lung tissue and including native epidermal growth factor retained from the lung tissue;
wherein the spleen extracellular matrix has a different concentration of epidermal growth factor than the lung extracellular matrix, and the lung extracellular matrix has a different concentration of elastin than the spleen extracellular matrix;
wherein the particles of spleen extracellular matrix and the particles of lung extracellular matrix range from about 1 nm to about 5 µm in diameter; and
wherein the composition is formulated for application onto or into a site of defect or wound of a patient via inhalation.

2. The composition of claim 1, wherein the spleen extracellular matrix further comprises at least one native growth factor retained from spleen tissue chosen from vascular endothelial growth factor, platelet-derived growth factor, fibroblast growth factor, or insulin-like growth factor.

3. The composition of claim 2, wherein each of the spleen extracellular matrix and the lung extracellular matrix comprises vascular endothelial growth factor, and the spleen extracellular matrix has a higher concentration of vascular endothelial growth factor than the lung extracellular matrix.

4. The composition of claim 2, wherein each of the spleen extracellular matrix and the lung extracellular matrix comprises platelet-derived growth factor, and the spleen extracellular matrix has a higher concentration of platelet-derived growth factor than the lung extracellular matrix.

5. The composition of claim 1, wherein the particles of spleen extracellular matrix and the particles of lung extracellular matrix range from about 1 nm to about 500 nm in diameter.

6. The composition of claim 1, further comprising at least one of an antimicrobial agent or a pharmaceutical agent.

7. The composition of claim 1, wherein the spleen extracellular matrix and the lung extracellular matrix are present in the composition in a 50-50 ratio.

8. The composition of claim 1, wherein the composition has a higher concentration of epidermal growth factor than vascular endothelial growth factor.

9. The composition of claim 1, wherein the particles of the spleen extracellular matrix include platelet-derived growth factor, and the composition has a higher concentration of vascular endothelial growth factor than platelet-derived growth factor.

10. The composition of claim 1, wherein the particles of the spleen extracellular matrix comprise about 3.6 ng/mg to about 5.8 ng/mg of epidermal growth factor.

11. The composition of claim 1, wherein the particles of the spleen extracellular matrix and the particles of the lung extracellular matrix each comprise native platelet-derived growth factor, and the spleen extracellular matrix has a different concentration of platelet-derived growth factor than the lung extracellular matrix.

12. The composition of claim 1, wherein the composition has a unimodal particle size distribution.

13. The composition of claim 1, further comprising a pharmaceutical agent or therapeutic agent.

14. The composition of claim 1, further comprising a steroid.

15. A composition comprising:
spleen extracellular matrix in particulate form, wherein the spleen extracellular matrix comprises native epidermal growth factor retained from spleen tissue; and
lung extracellular matrix in particulate form, wherein the lung extracellular matrix comprises native epidermal growth factor retained from lung tissue;
wherein the spleen extracellular matrix has a different concentration of epidermal growth factor than the second extracellular matrix, and the second extracellular matrix has a different concentration of elastin than the spleen extracellular matrix;
wherein the composition comprises about 6.1 ng/mg to about 12.5 ng/mg of epidermal growth factor;
wherein the particles of spleen extracellular matrix and the particles of lung extracellular matrix range from about 1 nm to about 5 µm in diameter; and
wherein the composition is formulated for application onto or into a site of defect or wound of a patient via inhalation.

16. The composition of claim 15, wherein the spleen extracellular matrix and the lung extracellular matrix are present in the composition in a 50-50 ratio.

17. The composition of claim 15, wherein the particles of spleen extracellular matrix and the particles of lung extracellular matrix range from about 1 nm to about 500 nm in diameter.

18. A composition comprising:
spleen extracellular matrix in particulate form, wherein the spleen extracellular matrix comprises native growth factors retained from spleen tissue, the native growth factors including epidermal growth factor, vascular endothelial growth factor, and platelet-derived growth factor; and
lung extracellular matrix in particulate form, wherein the lung extracellular matrix comprises native epidermal growth factor retained from lung tissue, the native growth factors including epidermal growth factor;
wherein the spleen extracellular matrix has a different concentration of epidermal growth factor than the lung extracellular matrix, and the lung extracellular matrix has a different concentration of elastin than the spleen extracellular matrix;
wherein the composition has a higher concentration of vascular endothelial growth factor than platelet-derived growth factor;
wherein the composition comprises about 6.1 ng/mg to about 12.5 ng/mg of epidermal growth factor;
wherein the particles of spleen extracellular matrix and the particles of lung extracellular matrix range from about 1 nm to about 500 nm in diameter; and
wherein the composition is formulated for application onto or into a site of defect or wound of a patient via inhalation.

19. The composition of claim 18, wherein the particles of spleen extracellular matrix and the particles of lung extracellular matrix have an average diameter of about 300 nm.

* * * * *